(12) United States Patent
Nilsson

(10) Patent No.: US 6,444,655 B1
(45) Date of Patent: Sep. 3, 2002

(54) GALACTOPYRANOSIDES AND THEIR USE

(75) Inventor: Kurt Nilsson, Lund (SE)

(73) Assignee: Procur AB, Lund (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,486

(22) PCT Filed: Dec. 23, 1996

(86) PCT No.: PCT/SE96/01756
§ 371 (c)(1),
(2), (4) Date: Jun. 19, 1998

(87) PCT Pub. No.: WO97/23637
PCT Pub. Date: Jul. 3, 1997

(30) Foreign Application Priority Data

| Dec. 21, 1995 | (SE) | 9504616-5 |
| Jan. 4, 1996 | (SE) | 9600058-3 |
| Jan. 24, 1996 | (SE) | 9600290-2 |
| Mar. 13, 1996 | (SE) | 9600994-9 |
| Apr. 2, 1996 | (SE) | 9601309-9 |
| May 11, 1996 | (SE) | 9601849-4 |
| May 15, 1996 | (SE) | 9601891-6 |
| May 19, 1996 | (SE) | 9601916-1 |
| Jul. 18, 1996 | (SE) | 9602844-4 |
| Aug. 20, 1996 | (SE) | 9603043-2 |
| Sep. 18, 1996 | (SE) | 9603434-3 |

(51) Int. Cl.[7] ............... A61K 31/702; C12P 19/14; C07G 3/00

(52) U.S. Cl. ............... 514/61; 514/23; 514/54; 514/62; 435/74; 435/99; 435/100; 536/4.1; 536/17.3; 536/17.9; 536/123; 536/123.13

(58) Field of Search ............... 435/74, 99, 100; 536/4.1, 17.3, 17.9, 123, 123.13; 514/61, 54, 23, 62

(56) References Cited

U.S. PATENT DOCUMENTS

| 4,137,401 A | | 1/1979 | Lemieux et al. |
| 4,918,009 A | * | 4/1990 | Nilsson ............... 435/73 |
| 5,651,968 A | * | 7/1997 | Good et al. ............... 424/140.1 |

FOREIGN PATENT DOCUMENTS

| EP | 0345732 | | 12/1989 |
| WO | WO930316 | | 2/1993 |
| WO | WO 93/03735 | * | 3/1993 |

OTHER PUBLICATIONS

Joziasse et al, Eur. J. Biochem. 191:75–83, 1990.*

* cited by examiner

Primary Examiner—Francisco Prats
(74) Attorney, Agent, or Firm—Smith, Gambrell & Russell

(57) ABSTRACT

The present invention relates to simplified synthesis, new carbohydrate-based products and practical use of different carbohydrate-based products. Examples of these are (Galα1-3Gal), GlcNAcβ1-3Gal, α- or β-glycosides thereof, Galα1-3Gal- containing tri-, or higher oligosaccharides, α- or β-glycosides thereof, GlcNAcβ1-3Gal containing tri-, tetra-, or higher oligosaccharides, and derivatives and/or α- or β-glycosides thereof, Galα1-3GalGlcNAcβ1-3Gal, α- or β-glycosides thereof, Galα1-3Galβ1-4GlcNAcβ1-3Galβ1-4Glc, or other higher oligosaccharides containing the Galα1-3Gal-structure, α- or β-glycosides thereof, modified carbohydrates, di-, tri-, oligo-, or polyfunctional products containing carbohydrate structures, and the use of the products for synthesis, affinity purification, diagnostic applications and therapy.

8 Claims, 7 Drawing Sheets

US 6,444,655 B1

GALACTOPYRANOSIDES AND THEIR USE

This is a 371 of International Application No PCT/SE96/01756, with an international filing date of Dec. 23, 1996, now abandoned with regard to the United States of America.

The present invention relates to simplified synthesis, carbohydrate-based products and practical use of different carbohydrate-based products. Examples hereof are (Galα1-3Gal), GlcNAcβ1-3Gal, α- or β-glycosides thereof, Galα1-3Gal-containing tri- or higher oligosaccharides, α- or β-glycosides thereof, GlcNAcβ1-3Gal containing tri-, tetra- or higher oligosaccharides, and derivatives and/or α- or β-glycosides of any of these, Galα-1-3GalGlcNAcβ1-3Gal, α- or β-glycosides thereof, Galα1-3Galβ1-4GlcNAcβ1-3Galβ1-4Glc or other higher oligosaccharides containing the Galα1-3Gal-structure, α- or β-glycosides thereof, modified carbohydrates, di-, tri-, oligo- or polyfunctional products containing carbohydrate structures, and the use of the products for synthesis, affinity purification, diagnostic applications and therapy.

During the last years, there has been a great interest in synthesis and application of so-called biologically active carbohydrates, which are present in humans, animals and plants especially in the form of glycoproteins, glycolipids, proteoglycans and glycoaminoglycans, within for example diagnostics and therapeutics. Examples of these carbohydrates are blood group related substances, for instance substances of the type blood group A and blood group B determinants, with the structures GalNAcα1-3(Fucα1-2)Galβ-, and Galα1-3(Fucα1-2)Galβ-, respectively. During the last years there has been a great interest in, for example, carbohydrate structures containing Galα1-3Galβ- since this type of structures has turned out to be of great importance in the binding of patogens causing infectious diseases in cattle (e.g. diarrhea), and as antigenic structures, e.g. different cancer cells express this epitope, and the Galα1-3Galβ1-4GlcNAc-epitope is of interest for vaccination against different types of cancer.

Also pig organs express the Galα1-3Galβ-epitope and longer carbohydrate structures containing this structure. Therefore, during the last few years there has been a considerable interest in potential xenotransplantations in connection with the use of carbohydrate structures which contain, for example, Galα1-3Galβ- and oligosaccharides which contain this structure, for example Galα1-3Galβ1-4GlcNAc and Galα1-3Galβ1-4GlcNAcβ1-3Galβ1-4Glc. This type of structures seems to be responsible for the primary antibody-mediated rejection response (hyperacute rejection; HAR) of transplanted pig organs to other species including humans.

The same problem will arise in a human- to -human transplantation if the organ donor has a different blood group than the recipient. This limits the availability of suitable donor organs, especially for patients in acute conditions.

In addition to the structures mentioned above, GlcNAcβ1-3Gal and tri-, tetra- or higher oligosaccharides which contain this structure, such as e.g. Galβ1-3GlcNAcβ1-3Galβ1-4Glc, are of interest as potential alternatives to antibiotics, because it is known that e.g. pathogenic respiratory bacteria bind to the respiratory tract via such carbohydrate structures. The possibility of inhibiting infections with such structures, or with derivatives thereof, is of considerable interest.

In addition to the therapeutic application there is a lot of interest in e.g. the above mentioned structures for the isolation or removal of cells, enzymes and proteins, employing e.g. affinity chromatography, where the structures are coupled to a separation material, such as agarose. It is very interesting to use such separation materials for isolation of proteins which have specificity towards the structures, e.g., glycosyltransferases (which use the saccharide structures as acceptor substrates), lectins, antibodies, and other proteins.

Also, the application of the structures as diagnostic reagents for determination of a cell (for example a pathogenic bacteria), an enzyme, an antibody, another carbohydrate-bound protein, is of considerable interest.

One example is the application in biosensors (e.g. BiaCore, Pharmacia). Here the carbohydrate structure can be bound to a surface, and the subsequent binding of a cell, an enzyme or a protein to the surface (with bound carbohydrate), results in an electric signal which is related to the degree of binding. As a result, both qualitative and quantitative measurements can be done. Another application is in ELISA (enzyme-linked immunosorbent assay). Here the carbohydrate structure can, e.g., be bound to microtiter wells on an ELISA-plate (e.g. via direct covalent binding to activated wells, for example from NUNC, Danmark), via a spacer molecule, or via conjugation to e.g. bovine serum albumin, which then can be bound to the microtiter wells. A sandwich-ELISA of the standard type can, for instance, then be carried out with such ELISA-plates, where the number of carbohydrate-specific cells, enzymes or proteins in a sample can be quantified with any of the standard methods which are used in ELISA (e.g. application of samples to carbohydrate-modified microtiter plates, followed by washing, application of enzyme-conjugate, e.g. peroxidase conjugated with carbohydrate, or antibody specific to the carbohydrate, followed by washing, addition of enzyme-conjugate and substrate, followed by measurement of the absorbance in the mikrotiter wells.

The main problem in the application of carbohydrates today, for example, in diagnostic applications, in down stream processing, for separation of cells, or proteins, or enzymes, in the vaccination against cancer, for specific removal of (xeno)antibodies from plasma in xenotransplantation employing relevant carbohydrate determinants as affinity ligands, and/or for neutralisation of the antibodies via addition of soluble carbohydrates or derivatives thereof, and for application in the prevention of infectious diseases, is to produce the adequate carbohydrate structures or derivatives thereof in pure form and in sufficient quantities. It is desirable to minimise the use of chemical methods, because they are cumbersome (e.g. multi-step synthesis) and result in side-reactions, resulting in the formation of for example mixtures of stereoisomers (α/β-mixtures). Thus, it would be very attractive to find a suitable method for the synthesis of the α1-3-linkage and the β1-3- linkage in the above mentioned structures.

The present invention describes a simplified synthesis of di- tri- and oligosaccharides, and glycosides and derivatives thereof, as for example (Galα1 -3Gal), α- or β-glycosides thereof, trisaccharides of the type Galα1-3Galβ1-4GlcNAc and other Galα1-3Gal-containing trisaccharides, α- or β-glycosides thereof, Galα1-3Galβ1-4GlcNAcβ1-3Gal, α- or β-glycosides thereof, Galα1-3Galβ1-4GlcNAcβ1-3Galβ1-4Glc or other higher oligosaccharides containing the Galα1-3Gal-structure, α- or β-glycosides thereof, and modified carbohydrates containing α1-3-bound galactopyranosyl-galactopyranose and modified β-glycosides thereof, GlcNAcβ1-3Gal, derivative thereof, GlcNAcβ1-3Gal containing tri-, tetra-, or higher oligosaccharides, as for example Galβ1-3GlcNAcβ1-3Gal and Galβ1-3GlcNAcβ1-3Galβ1-4Glc and derivatives and/or α- or β-glycosides thereof.

The terms derivative or modified carbohydrate mean structures where one or more of the hydroxyl groups or the —NAc group in the saccharides are substituted with an organic or inorganic group. Examples of organic and inorganic groups are given in the description below.

Figure 1:
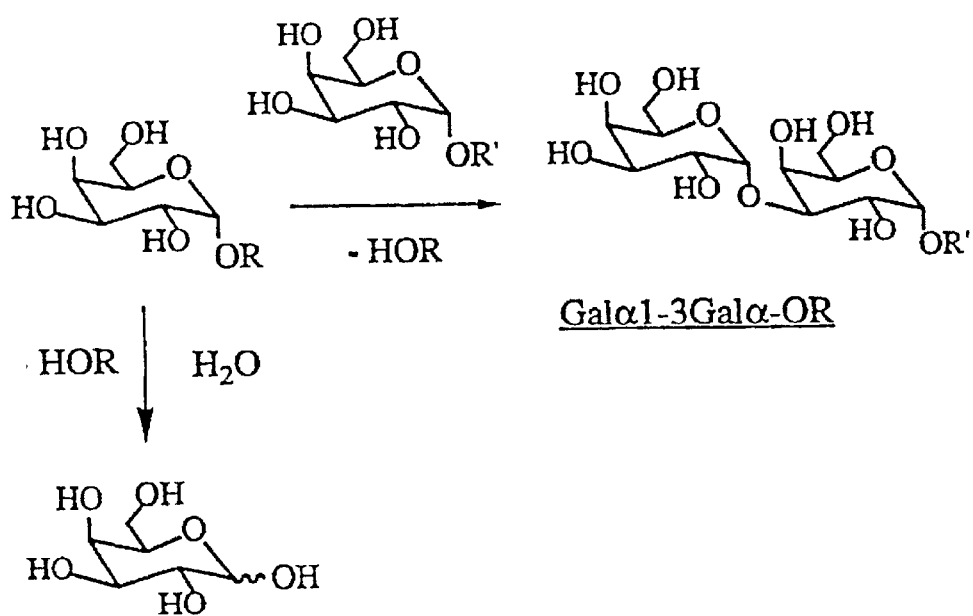
FIG. 1 depicts an example of a transglycosylation according to the invention.

One component in the method according to the invention relates to that a naturally existing glycosidase, (EC 3,2), or a chemically modified, or a variant thereof modified via recombinant technique, is used in, for example, a transglycosylation reaction. Below are given examples of the use of e.g. α-galactosidase for the production of the α-glycoside Galα1-3Galα-OR, where R is an aryl group, which can be chemically transformed to the desired final product. The first reaction is carried out with a so-called transglycosylation reaction of the type shown in FIG. 1.

In this reaction, α-galactosidase is used as catalyst. According to the invention, another α- or β-endo- or exo-glycosidase, such as α- or β-glycosidases of the type hexosaminidase, glucuronidase, xylosidase, mannosidase, sialidase, glucosaminidase, galactosaminidase, glucosidase (where the name gives the donor specificity), can be used. Products of the following type are obtained:

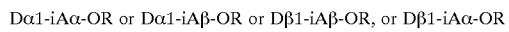

Dα1-iAα-OR or Dα1-iAβ-OR or Dβ1-iAβ-OR, or Dβ1-iAα-OR where i gives the binding position to the acceptor, and D is derived from the donor and A from the acceptor, the latter containing mono-, di-, or oligosaccharide substances.

Galα1-3Galα-OR is a non-limiting example. Other non-limiting exemples are Galβ1-3Galβ-OR, Galβ1-3GlcNAcβ-OR, Galβ-1-3GalNAcβ-OR, GalNacβ1-3Galβ-OR, Manα1-2Manα-OR, etc, produced in the same way as Galα1-3Galα-OR, but using another donor, acceptor, and glycosidase, but with the same type of acceptor aglycon (OR in these cases).

For example, in the case Galβ1-3Galβ-OR, a β-galactoside is used as a donor, Galβ-OR as acceptor and β-galactosidase as enzyme. These are easily chosen by the expert and this does not limit the scope of the invention.

Other regioisomers are often obtained, such as for instance 1-2 and 1-6-bound products, but these can be separated from the desired 1-3-bound product using, for example, column chromatography (Sephadex G10 or G15, or C18 chromatography), before or after modification of the product, or using enzymatic hydrolysis of the side-products with one, or two different, glycosidases which have another regioselectivity than the enzyme used in the reaction above.

As enzyme source use can be made of animal tissue, plants, or a micro-organism, e.g. in the production of Galα1-3Galα-OR, α-galactosidase from coffee beans, or from for example *Aspergillus oryzae*, or from *Aspergillus niger*, which contain high amounts of the enzyme. Other suitable enzyme sources, which give a high amount of α1-3-bound product, can also be chosen by the expert. The reaction can, for example, be carried out with modified, or immobilised, or unmodified enzyme, in buffered water (e.g. with a pH in the interval 4-8), or in a mixture of water and organic solution, at a suitable temperature (e.g. in the interval 0 to 80 degrees C.) and with suitable concentrations of substrate (e.g. in the interval 50 mM to 1 M) with a reaction time, which is suitable to get optimal product concentration (the latter can be followed by e.g. HPLC).

The reaction conditions and type of enzyme (type of modification, such as chemical modification, cross-linking, polyethylene glycol modified, type of immobilisation, type of unmodified enzyme, or type of modified enzyme, and/or type of enzyme produced with recombinant, or genetic engineering technology) are chosen and produced by the expert and do not limit the scope of the invention.

The degree of purity of the enzyme is not critical, e.g. freeze-dried enzyme preparations, obtained after homogenisation of coffee beans, extraction with buffer, precipitation of the homogenate with ammonium sulphate (e.g. 50–70 % saturation), dialysis and freeze-drying, can be used. When required, the enzyme can be used in a less pure form than in the example above, or in a more pure form, e.g. as obtained after column chromatography based on size separation (e.g. of the above mentioned freeze-dried preparation using Sephadex® G75—which removes major parts of discoloration in the less purified enzyme preparations). A further isolated enzyme preparation, obtained with e.g. affinity chromatography employing, e.g., a separation material which contains an (α-galactoside immobilised via a so-called spacer, can also be used according to the invention. This does not limit the invention. An immobilised enzyme is obtained by choosing, for example, tresyl-activated carrier (e.g. agarose or cellulose), N-hydroxysuccinimide-activated carrier, e.g. agarose (e.g. from Pharmacia, such as e.g. activated CM-Sepharose®, e.g. NHS-activated Sepharose® Fast Flow) or another method for immobilisation of e.g. the above mentioned freeze-dried enzyme preparation, or of the further isolated enzyme preparation. This is easily carried out by the expert and does not limit the application of the invention. The immobilised enzyme can be used in, e.g., a batch-wise reaction or in a column (for continuous synthesis). Nothing of this will limit the scope of the invention.

Affinity chromatography with monosaccharides as affinity ligands has been mentioned above as an example of a method for (partial) purification of the enzyme. According to the invention, also carbohydrate-based affinity ligands can be used which contain the disaccharide sequence, or the glycosidic linkage, that the enzyme shall synthesise, or the carbohydrate ligand can contain the undesired carbohydrate sequence. This is used in order to make it possible to achieve affinity separation of different iso-enzymes from the same enzyme source which give different regioselectivity in the same synthesis. Thus many enzyme sources contain at least two different isoenzymes of e.g. α-galactosidase and β-galactosidase. In some cases it can be advantageous to separate these, in order to get, e.g., a higher selectivity in hydrolysis or in transglycosylation reactions using the enzymes.

When α-galactosidase is used for synthesis of Galβ1-3Gal-R, one can obtain, e.g., Galα1-3Galβ-Y, where Y in this case is a group suitable for coupling to the separation material. Many possibilities for Y and the separation material exist and do not limit the scope of the invention. Thus, for example, Galα1-3Galα-OPhNH$_2$-p or Galα1-3Galβ1-4Glcβ-OPhNH$_2$-p can be used as carbohydrate-based affinity ligands for coupling to e.g. N-hydroxy-succinimide-activated carboxyl groups on e.g. agarose or other separation materials. The resulting material can be used for isolation of, in this case, α-galactosidase. The hydrolysisis of the affinity ligand can be minimized by, e.g., using a low temperature or a pH which lies outside the pH-optima for the enzyme, such as pH 8 in the case of (α-galactosidase from coffee beans.

The enzyme can be eluted in many ways, e.g. non-specifically with salts, or more specifically with e.g. galactose or Galα1-3Gal. Another analogous example is β-galactosidases, e.g. from bovine testes, where it is possible to use e.g. Galβ1-3GlcNAc-spacer as an affinity ligand for isolation. An alternative to the above is to bind the glycosidase in question to some type of affinity material e.g. with immobilised monosaccharide glycoside as affinity ligand, and then elute with e.g. the carbohydrate structure that will be synthesised/hydrolysed with the enzyme.

Figure 2:
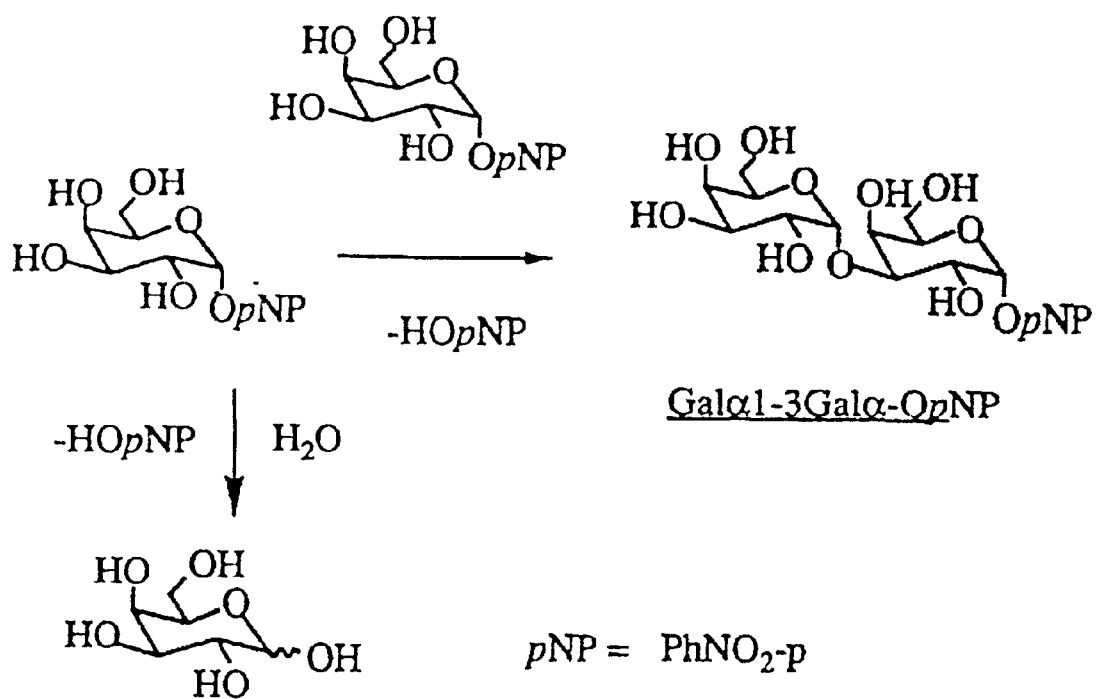
FIG. 2 depicts an example of a glycosidase-catalyzed reaction according to the invention wherein RO=p-nitrophenyl.
Figure 3:
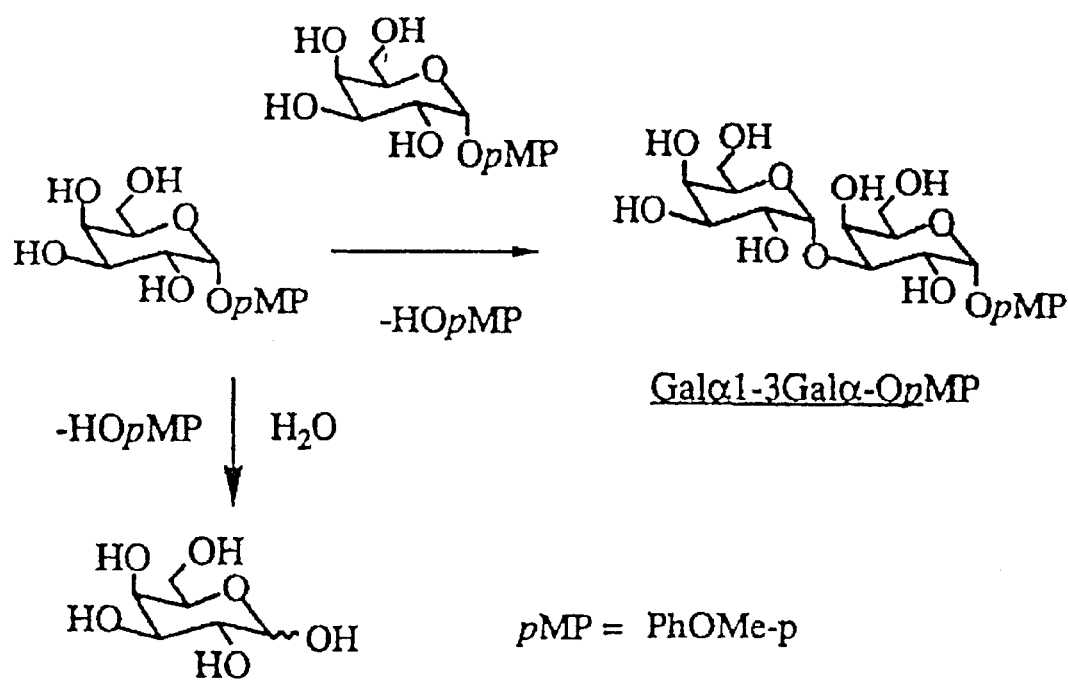
FIG. 3 depicts an example of a glycosidase-catalyzed reaction according to the invention wherein R'O=p-metoxyphenyl.

In the glycosidase reactions mentioned above, R=R' or R and R' can be different. Examples of this are given in FIG. 2 (RO=p-nitrophenyl) and in FIG. 3 (R'O=p-metoxyphenyl) for the case α-galactosidase.

The product in the reactions above can then, according to the invention, be used to make the free saccharides from the produced glycosides.

Figure 4:
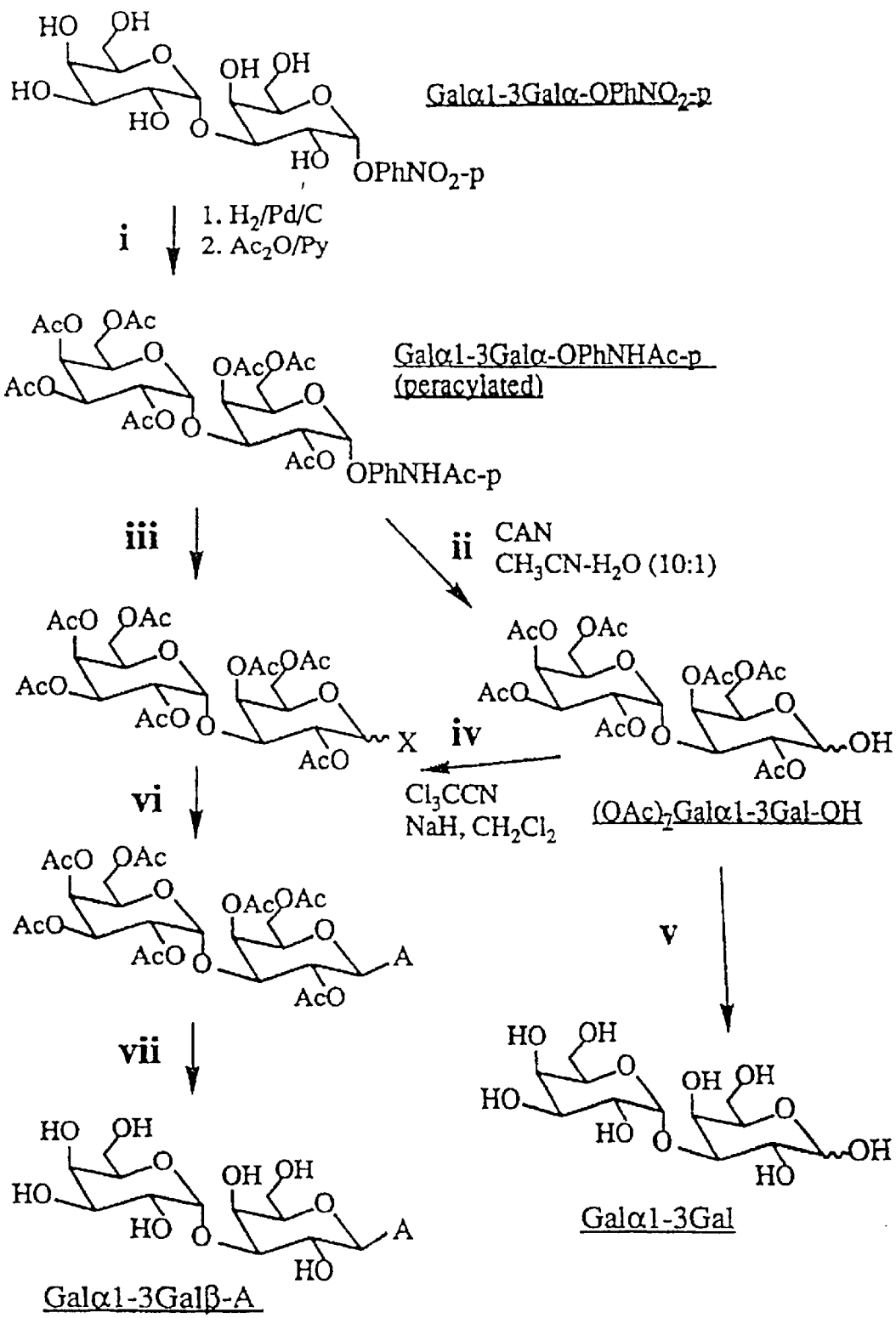
FIG. 4 depicts an example of the production of Galα1-3Gal by chemical methods.
Figure 5:
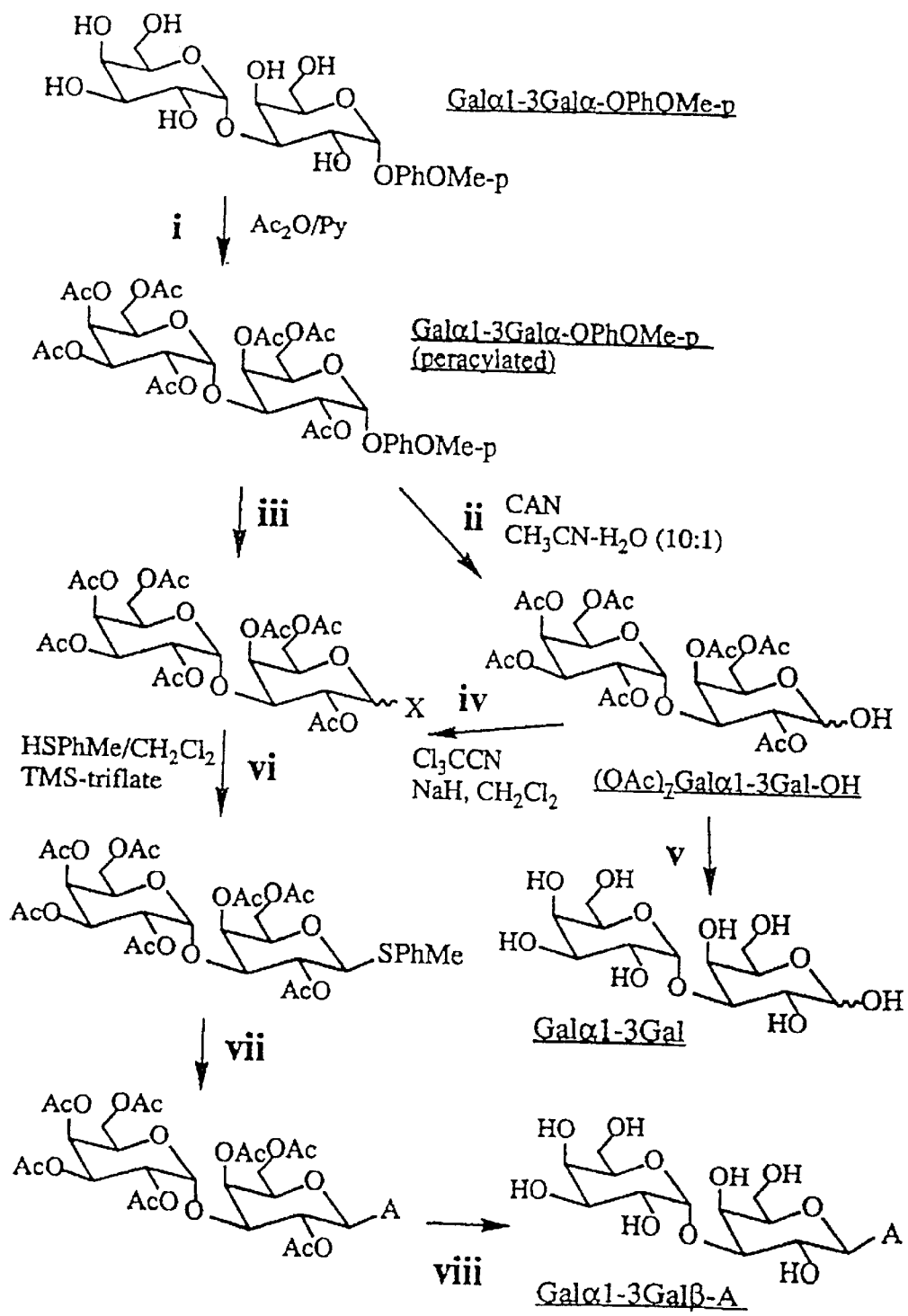
FIG. 5 depicts an example of the production of Galα1-3Galβ-A by chemical methods.

This will be exemplified, as non-limiting examples, for the production of Galα1-3Gal or Galα1-3Galβ-A, employing e.g. chemical methods according to e.g. the principles in FIGS. 4 and 5. In the reaction schemes in these Figures, it have been exemplified how the structures can be changed to Galα1-3Gal or Galα1-3Galβ-A. The given examples of reagents should be regarded as non-limiting examples and other suitable reagents can be chosen by the expert. Examples of —X are —SEt, —SPh or —SPhMe—p after further reaction with thioethanol, thiophenol or HSPhMe respectively.

Figure 6:
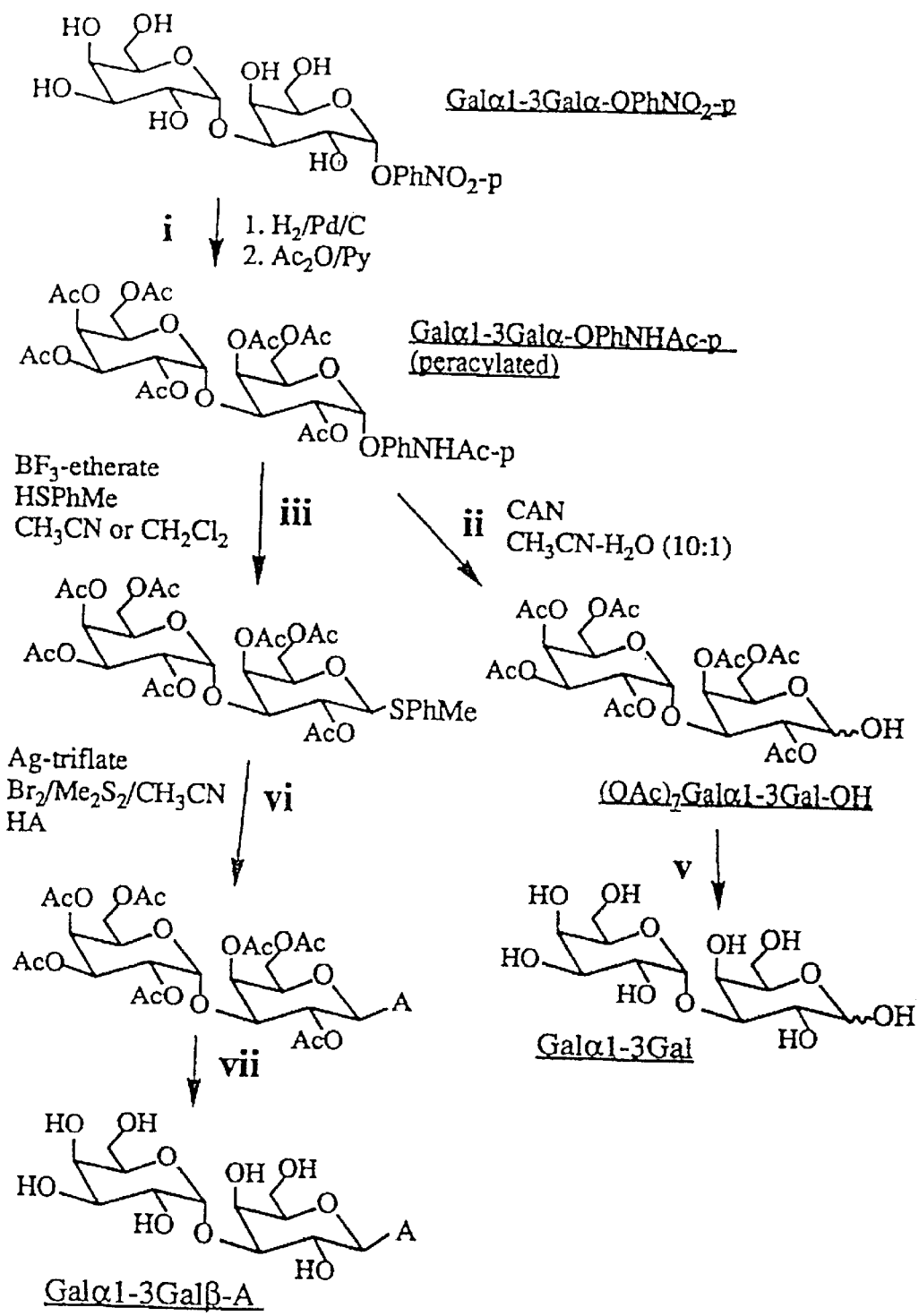
FIG. 6 depicts an example of changing Galα1-3Galα-OPhNO$_2$-p to β-glycosides.

Further non-limiting examples of changing Galα1-3Galα-OPhNO$_2$-p to β-glycosides and higher oligosaccharides of disaccharides (symbolised with Galα1-3Galβ-OR) via change of the α-PhNHAc glycoside to the β-SPhMe glycoside are given in FIG. 6.

In reaction vi in FIG. 6, Ag-triflate has been mentioned but this reagent can be replaced by e.g. N-iodosuccinimide, or N-bromosuccinimide. Examples of A are mentioned below.

As a more specific example, it can be mentioned that in the synthesis of trisaccharide derivatives, A is e.g. a monosaccharide derivative which contains e.g. a 2-deoxy-2-amino-D-glucopyranose-group, which is protected e.g. at least in the 6-position with e.g. a benzoyl group (non-limiting example), and in the 1-position with a suitable organic group, such as e.g. (non-limiting examples) β-bound —OCH$_2$CH$_2$PhNO$_2$-p or —OPhNH—CO—R, where —CO—R can be e.g. an organic group suitable for temporary protection of the NH-group, or can be a group which, after chemical modification, can be used for covalent binding to a protein, a peptide, a separation material or to a low molecular organic or inorganic group. In these examples of A, the 2-amino-position can be modified with an acetyl group or another acyl group containing substance, of which the groups phthalimido- and trichloroethoxycarbonyl are non-limiting examples. In these examples of A, the protection groups can be removed with conventional chemical methods (and/or the nitro-group in the 1-position is reduced), whereupon the product can be used in the applications exemplified below. If only the 6-, 2- and 1-positions are protected in the example above, both the β1-4 linkage (predominant in most cases) and the β1-3 linkage, between the Galα1-3Gal and the 2-deoxy-2-amino-D-glucopyranose groups, are obtained. These two products can be separated, or a mixture of the products can be used in the applications below.

In FIGS. 4 and 6, Pd/C is mentioned for reduction, but this can be replaced by other reduction reagents which are more suitable for bulk synthesis. Non-limiting examples are Zn/HOAc, used e.g. after acetylation, which gives amino compound, which can be used for application according to the invention (see below), or which can be acylated and used as ii or iii in FIGS. 4 and 6.

Instead of production of the β-SPhMe glycoside via Galα1-3Galα-OPhNO$_2$-p, according to the invention, e.g. Galα1-3Galα-SEt can be used for the same purpose as the β-SPhMe glycoside in FIG. 6. Galα1-3Galα-SEt is obtained, e.g. via the same type of glycosidase-reaction mentioned in FIG. 2 but with Galα-SEt as acceptor and e.g. raffinose or Galα-OPhNO$_2$-p as donor. Also, Galα1-3Galα-OBn can be of interest for e.g. production of Gal 1-3Gal, or of glycosides and higher oligosaccharides, or for direct use as inhibitor according to the description below. For production of Galα1-3Galαα-OBn, Galα-OBn is used as acceptor instead of Galα-SEt. Also, Galα1-3Galα-OMe and other Galα1-3Galα-glycosides, or Galα1-3Gal-containing saccharides made with enzymatic (e.g. with glycosidase according to FIG. 2 but with Galα-OMe or other glycoside as acceptor), and/or with chemical methods, can be of interest according to the invention, for e.g. direct use, according to the invention, as inhibitor, for analyses or in separation materials (see below). According to the invention, for some of these applications, e.g. saccharides of the type Galα1-3Galα-R are useful in general, where R is an O, N, C- or S-glycosidically bound organic group, such as a group which contains, for example, one or more of the general groups aliphatic hydrocarbon, aromatic hydrocarbon (phenyl, etc), amino group, carboxyl group, ceramide group, sulphate group, amino acid, peptide, protein, monosaccharide, disaccharide, oligosaccharide, polymer, lipid, steroid, nucleic acid, nucleotide, or R can be an inorganic group. If R is an organic group, R can be e.g. an alkyl group, aliphatic group, aromatic group, saccharide, lipid, amino acid, peptide, protein, or contain groups from more than one of these groups. Examples of alkyl group are groups of the type —(CH$_2$)$_n$CH$_3$, where n is an integer larger than or equal to zero, and preferably n is an integer in the interval 0–20. Non-limiting examples of R=saccharides, is N-acetyl-glucopyranose-group (GlcNAc-group, e.g. bound via the 4-position in GlcNAc), a glucopyranosyl group (Glc-group), another monosaccharide, a disaccharide containing one or more of these groups or a derivative thereof, an oligosaccharide containing one or more of these groups or a derivative thereof, a polymer based on e.g. agarose, cellulose, polystyrene, polyacrylamide, polyvinylalcohol, polyetyleneglycol (see e.g. Shearwater polymers' catalogue for non-limiting examples of polyethylene glycol derivatives which can be used, according to the invention, for production of mono-, di-, or multifunctional products,—in the latter case e.g. of the type tresyl-Star-PEG where the carbohydrate can be bound e.g. via an amino group containing spacer, which is bound as aglycon to the sugar, see further examples below), etc. Examples of amino acids are asparagine, serine, threonine, etc. Examples of peptides are peptide containing an asparagine, serine, and or threonine residue, etc, bound to the saccharide. —The same principles and methods according to the invention mentioned above, can also, according to the invention, be used for synthesis of other di-, tri- and oligosaccharides, and derivatives and analogues thereof, from the above mentioned Dα1-iAα-OR or Dα1-iAβ-OR or Dβ1-iAβ-OR, or Dβ1-iAα-OR type of compounds.

In the enzymatic synthesis via e.g. the α-galactosidase-catalysed synthesis above, use is made as acceptor of any of Galα-R, or (6-R')Galα-R, or (6-R',2-R")Galα-R, where R. R', and R" in this case symbolise an organic or inorganic group. Non-limiting examples of —R are an aliphatic or aromatic group, for instance —SEt, —O(CH$_2$)$_n$CH$_3$ (n=an integer between e.g. 0 and 12), —O(CH$_2$)$_n$COOR (R=H, or an aliphatic or an aromatic organic group; n=an integer between e.g. 0 and 12), —OPh, —OCH$_2$Ph (—OBn), —OPhNO$_2$-p, —OPhOMe-p, to Gal bound Glc (e.g. lactose is used as acceptor), GlcNAc, GlcNTeocβ-SEt or another saccharide, or a lipid, amino acid, peptide or a derivative thereof, for instance L-serine or L-threonine, or a derivative thereof, or a peptide containing any of these. Non-limiting examples of R' and R" in this connection is an inorganic or organic group. Non-limiting examples of this are sulphate, carboxyl and phosphate group, deoxy group (—OH is replaced by —H), ester group (for instance benzoyl, acetyl), allyl-, benzyl- or p-methoxybenzyl group.

The donor and acceptor substances above are commercially available or are easy to get or can easily be synthesised by the expert and this does not limit the scope of the invention.

R above can be mono-, di-, tri-, oligo-, or multi(poly) functional (see for example the above mentioned examples of R), or can be modified to become di- tri-, oligo-, or multi-(polyfunctional), meaning that one, two, three or more saccharide-groups are glycosidically bound to a different or the same type of functional groups in R, e.g. products of for example the type (Galα1-3Galα-)$_n$—R or (n is an integer equal to or larger than 1) can be produced by the method according to the invention. This can be advantageous if products with high affinity towards, for instance, a galabiose-binding protein (such as antibodies, in e.g. the xenoapplications).The production of such products does not limit the scope of the invention but can easily be carried out by an expert employing the method according to the invention.

A in the Figures for producing Galα1-3Galβ-A symbolises an O-, N-, S-, or C-, β- or α-glycosidically bound substance, containing for example one or more of the general groups of aliphatic hydrocarbon, aromatic hydrocarbon, amino group, carboxyl group, sulphate group, amino acid, peptide, protein, monosaccharide, disaccharide, oligosaccharide, polymer, lipid, such as ceramide, steroid, nucleic acid, nucleotide.

Non-limiting examples of A are a substance containing a β-glycosidically bound N-acetyl-glucopyranose-group (GlcNAc-group, for example bound via the 4-position in GlcNAc), a glucopyranosyl group (Glc-group), another monosaccharide, a disaccharide containing some of these or a derivative thereof, an oligosaccharide containing one or some of these groups or a derivative thereof, a polymer based on e.g. agarose, cellulose, polystyrene, polyacrylamide, polyvinylalcohol, polyethylene glycol (see e.g. Shearwater polymers' catalogue for non-limiting examples of polyethylene glycol derivatives which can be used according to the invention for production of mono-, di-, or multifunctional products, in the latter case for example of the type tresyl-Star-PEG, where the carbohydrate can be bound for example via an amino group containing spacer bound as aglycon to the sugar, see below), etc. Examples of amino acids in connection with A are asparagine, serine, threonine, etc. A can contain for example an alkyl group, such as (CH$_2$)$_n$CH$_3$(n=0–18, for example), or an aromatic group. See above for other non-limiting examples of A.

In the case where A contains the group GlcNAcβ-R''' or GlcNAcβ1-3Gal, e.g. substances of the type Galα1-3Galβ1-4GlcNAcβ-R''', Galα1-3Galβ1-4GlcNAcβ1-3Gal, Galα1-3Galβ1-4GlcNAcβ1-3Galβ1-4Glc, Galα1-3Galβ1-4GlcNAcβ1-3Gal-R''', or Galα1-3Galβ1-4GlcNAcβ1-3Galβ1-4Glc-R''' will be produced according to the invention. It is possible to use, for example, chemical and/or enzymatic reactions for producing GlcNAcβ-R''', GlcNAcβ1-3Gal or GlcNAcβ1-3Galβ1-4Glc, or a derivative thereof, which can then be used as acceptor in the scheme above, with for example Galα1-3GalβSEt or Galα1-3GalβSPh as donor (R''' above symbolises an α- or β-bound substance exemplified in the previous paragraphs).

An example of such an enzymatic reaction is the use of a glycosidase (EC 3.2.) belonging to the subgroup N-acetyl-β-D-glucosaminidase (alternatively called β-hexosaminidase) or a glycosyltransferase (EC 2.4) belonging to the subgroup of UDP-GlcNAc-depending N-acetyl-β-D-glucosaminyltransferases which are active with galactose, or galactoside, or galactosyl-saccharide as acceptor.

In the case of glycosidase, the equilibrium reaction is used (non-activated donor) or preferably a kinetic reaction with donor of the type GlcNAcβ-R, where R is a glycosidically bound organic or inorganic group. Non-limiting examples of —R in this context are —OPh, —OPhNO$_2$-p and —OPhOMe-p and β1-4 bound GlcNAc or chitobiose. As acceptor, use is made of galactose, or a derivative thereof as for example (but non-limiting), Galβ-R or (6-R')Galβ-R, or (6-R',2-R")Galβ-R, where R. R', and R" in this context symbolise an organic or inorganic group. Non-limiting examples of —R are an aliphatic or aromatic group, as for example —SEt, —O(CH$_2$)$_n$CH$_3$ (n=an integer between for example 0 and 12), —O(CH$_2$)$_n$COOR (R=H, or an aliphatic or an aromatic organic group; n=an integer between for example 0 and 12), —OPh, —OCH$_2$Ph (—OBn), —OPhNO$_2$-p, —OPhOMe-p, β1-4-bound Glc or other saccharide, an amino acid, peptide or a derivative thereof, as for example L-serine or L-threonine, or a derivative thereof, or a peptide containing some of these. A non-limiting example of R' and R" in this context is an inorganic or organic group. Non-limiting examples hereof are sulphate-, carboxyl- and phosphate group, deoxy group (—OH is replaced by —H), ester group (for example benzoyl, acetyl), allyl-, benzyl- or p-methoxy-benzyl group.

The above mentioned donor and acceptor substances are commercially available or are easily synthesised by the expert and this does not limit the scope of the invention.

The source of the glycosidase is chosen by the expert and does not limit the scope of the invention. A non-limiting example of suitable enzyme sources is N-acetyl-β-D-glucosaminidase (alternatively called β-hexosaminidase) from *Aspergillus oryzae* or from *Chamelea gallina*.

Below, non-limiting examples of glycosidase-catalysed enzyme reaction according to the invention are illustrated (all structures according to IUPAC-rules, sugar in D-pyranose configuration):

a) GlcNAcβ-OPhNO$_2$-p + Galβ-OMe  HOPhNO$_2$-p

-continued

GlcNAcβ1-3Galβ-OMe b) GlcNAcβ-OPhNO$_2$-p + (6-Bn)Galβ-SEt $\xrightarrow{\text{—HOPhNO}_2\text{-p}}$
GlcNAcβ1-3(6-Bn)Galβ-SEt c) GlcNAcβ-OPhNO$_2$-p + (6-Ac)Galβ-SEt $\xrightarrow{\text{—HOPhNO}_2\text{-p}}$
GlcNAcβ1-3(6-Ac)Galβ-SEt d) GlcNAcβ-OPhNO$_2$-p + (6-Ac)Galβ-OBn $\xrightarrow{\text{—HOPhNO}_2\text{-p}}$
GlcNAcβ1-3(6-Ac)Galβ-OBn e) GlcNAcβ-OPhNO$_2$-p + (6-Ac)Galβ-OPhNO$_2$-p $\xrightarrow{\text{—HOPhNO}_2\text{-p}}$
GlcNAcβ1-3(6-Ac)Galβ-OPhNO$_2$-p f) GlcNAcβ-OPhNO$_2$-p + (6-Ac,2Ac)Galβ-OMe $\xrightarrow{\text{—HOPhNO}_2\text{-p}}$
GlcNAcβ1-3(6-Ac,2Ac)Galβ-OMe g) GlcNAcβ-OPhNO$_2$-p + HOR′″ $\longrightarrow$ GlcNAcβ-OR′″.

Figure 7:
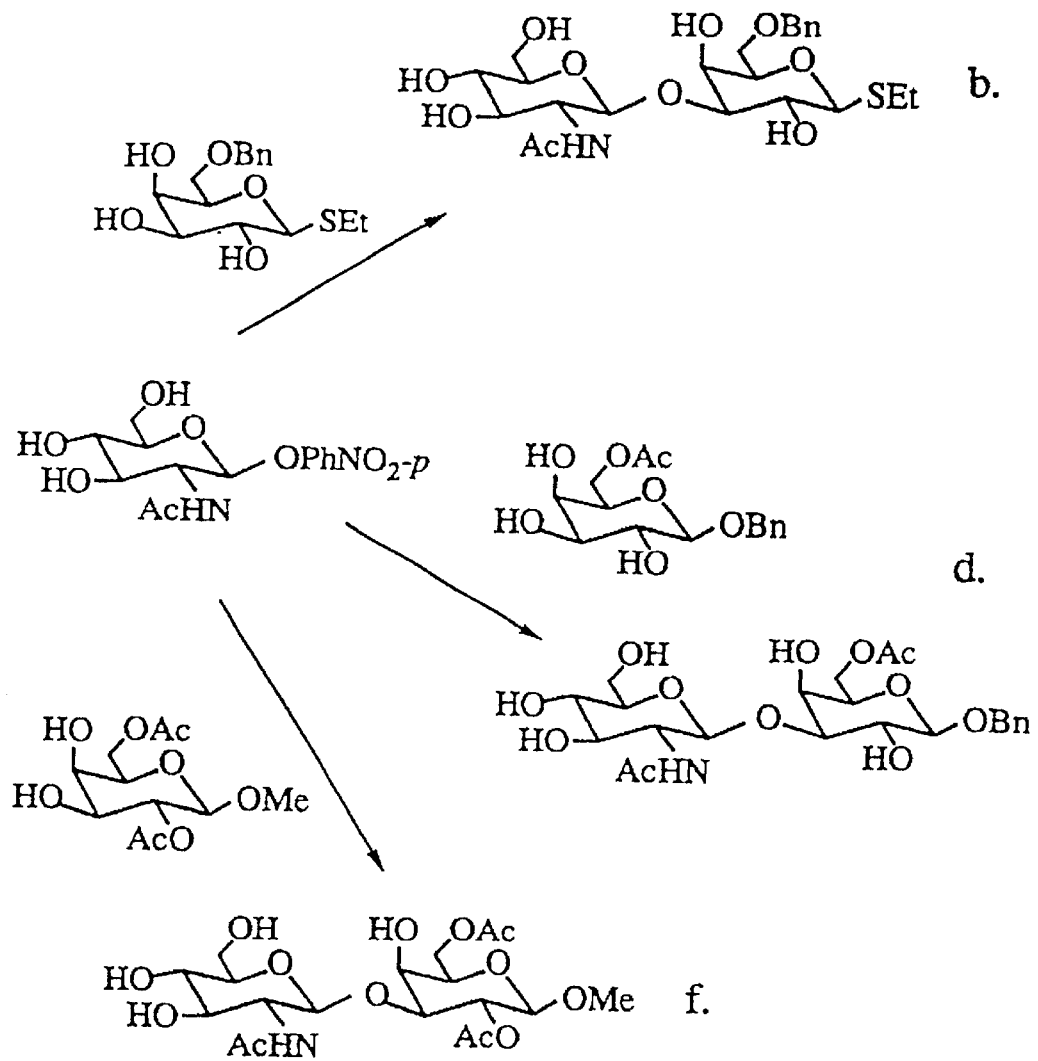
FIG. 7 depicts examples of glycosidase-catalyzed reactions according to the invention.

For the purpose of further clarification, see the illustration of the reactions b, d, f with molecular structures according to FIG. 7.

In the glycosidase-reactions above, hydrolysis is obtained as a side reaction, partially of donor and partially of produced product. This is well-known to the expert and does not limit the scope of the invention. The reaction is followed by HPLC and/or TLC, and/or in the examples above, by measurement of produced p-nitrophenol (abs 405), so that the reaction is stopped at the maximum product yield, using, for example, a brief heat treatment (for example in the interval 70–90° C. during 3–5 minutes), after which the product is isolated. The isolation of the product can be achieved with one or several of the methods: extraction (for example using one or some of methylene chloride, ethyl acetate, butanol), precipitation, or chromatography (for example Sephadex®, or silica as the solid phase), using standard conditions, which does not limit the scope of the invention. In the case where another regioisomer is produced, e.g. in the first reaction illustrated above, this regioisomer can be removed by, for example, chromatography, and/or by using a second enzymatic reaction with a hexosaminidase which specifically hydrolyses this regioisomer.

As an alternative to glycosidase can, as mentioned above, be used with UDP-GlcNAc as donor and Gal-substance as acceptor, for example of the type mentioned above for the hexosaminidase reactions.

GlcNAcβ1-3Gal containing structures prepared as stated above can, in one embodiment of the invention, be used for producing derivatives of the mentioned structures or for chemical synthesis of for example GlcNAcβ1-3Galβ1-4Glc (e.g. using peracetylated GlcNAcβ1-3GalβSEt as donor). Any of GlcNAcβ1-3Gal, GlcNAcβ1-3Galβ1-4Glc or derivatives of GlcNAcβ1-3Gal or of GlcNAcβ1-3Galβ1-4Glc, can then be used as acceptor for β-galactosidase-catalysed reaction with lactose or Galβ-R as donor (aglycon in this kinetic reaction is of the same type as mentioned above for kinetic reactions with galactosidase or hexosaminidase). Examples of such reactions are given below:

a) Galβ-OPhNO$_2$-p + GlcNAcβ1-3(6-Ac)Galβ-SEt $\xrightarrow{\text{—HOPhNO}_2\text{-p}}$
Galβ1-3GlcNAcβ1-3(6-Ac)Galβ-SEt b) Lactose + GlcNAcβ1-3(6-Ac)Galβ-OBn $\xrightarrow{\text{—Glucose}}$
Galβ1-3GlcNAcβ1-3(6-Ac)Galβ-OBn c) Lactose + GlcNAcβ1-3Galβ-OBn $\xrightarrow{\text{—Glucose}}$
Galβ1-3GlcNAcβ1-3Galβ-OBn d) Lactose + GlcNAcβ1-3Galβ1-4Glc $\xrightarrow{\text{—Glucose}}$
Galβ1-3GlcNAcβ1-3Galβ1-4Glc An example of enzyme source is bovine testes, but other enzyme sources which give the desired result can also be chosen by the expert and do not limit the scope of the invention. Before use, the enzyme can first be partially purified by using homogenisation, in for example sodium phosphate buffer, and precipitation with ammonium sulphate. The precipitate can then for example be dialysed against a suitable buffer and the enzyme preparation can then be immobilised according to what has been mentioned in other passages in the description. Isolation of the desired saccharide product can be done, for example, as has been mentioned above for the two other types of glycosidase-catalysed reactions.

The enzyme (of above mentioned types) can be immobilised before use, which facilitates: recovery and reuse of the enzyme, use in a column reactor (continuous synthesis). Non-limiting examples of immobilisation is the immobilisation to hydroxylgroup-containing materials (agarose, Sepharose®, cellulose, etc), which have been activated with for example tresyl chloride (which gives reactive tresylate esters which react with amino groups in the enzyme and thereby a covalent linkage between the enzyme and the material is produced). The immobilisation can carried out at, for example, room temperature and at a pH of, for example, 6.5, 7, 7.5 or 8. The enzyme can also be modified in other ways e.g. with chemicals (e.g. a cross-linker, or polyetylene glycol, PEG: for example tresyl- or NHS-activated PEG) or modified via a recombinant technique.

The enzyme, or the immobilised enzyme, or the modified enzyme, can be used in the solvents where it is active, preferably in buffered water (as a non-limiting example often from pH 4, 4.5, 5 or 5.5 to 6, 6.5, 7, 7.5 or 8), or in a water-organic solvent mixture (with the proper concentration and the type of solvent chosen by the expert), and at the proper temperature chosen by the expert (as non-limiting examples often from 4, 10, room temperature, 30 degrees Celcius to 35, 40, 45, 50, 55, 60, 65 70 or 80 degrees Celsius, the latter case especially when employing thermostable enzyme, or at high substrate concentrations). This does not limit the scope of the invention. The proper conditions are chosen by the expert. In the glycosidase-catalysed transglycosylation-reactions above, —F can also be chosen as aglycon in the donor and/or acceptor substance, meaning that F-glycosides can be obtained, which can be used for further synthesis by the expert.

According to the invention, the products which are synthesised as above can, after the expert has chosen the chemical modification, be used as donor and acceptor substances to form, for example, products of the type Galα1-3Galβ1-4GlcNAcβ1-3Gal, Galα1-3Galβ1-4GlcNAcβ1-3Galβ1-4Glc Galα1-3Galβ1-4GlcNAcβ1-3Gal-R′″, or Galα1-3Galβ1-4GlcNAcβ1-3Galβ1-4Glc-R′″ with for example peracetylated Galα1-3Galβ-SEt as the donor. This reaction is carried out by the expert using chemical methods and does not limit the scope of the invention.

For example, the disaccharide product GlcNAcβ1-3(6,2-Ac)Galβ-OMe is benzoylated (for example with benzoyl chloride/pyridine) in the 6-position of the GlcNAc-unit, and is then reacted with peracetylated Galα1-3Galβ-SEt in the presence of a suitable catalyst (for example Ag-triflate) in a suitable solvent (for example acetonitrile or dichloromethane). There is formed (2,3,4,6-Ac)Galα1-3(2, 4,6-OAc)Galβ1-4(6-Bzl)GlcNAcβ1-3(6-,2-Ac) Galβ-OMe (together with (2,3,4,6-Ac)Galα1-3(2,4,6-OAc)Gal β1-3(6-Bzl)GlcNAcβ1-3(6-,2-Ac)Galβ-OMe, which can be separated by chromatography, if desired). After removal of acetyl groups and benzoyl groups (for example with catalytic amount of sodium methoxide in methanol) one obtains efter purification (chromatography and/or precipitation) Galα1-3Galβ1-4GlcNAcβ1-3Galβ-OMe. If desired, (2,3,4,6-Ac) Galα1-3(2,4,6-Ac)Galβ1-3(6-Bzl)GlcNAcβ1-3(6-,2-Ac) Galβ-OMe can also be reacted in the same manner, and thereby one also obtains in the latter reaction Galα1-3Galβ1-3GlcNAcβ1-3Galβ-OMe. Instead of —OMe as the aglycon in these reactions, other aglycons can be used as mentioned above. A non-limiting example of this is βOPhNO$_2$-p which has the useful property that it can be easily reduced to βOPhNH$_2$-p, which is a suitable group for conjugation to other molecules (see below).

The structures mentioned above can also according to the invention be synthesised by using a galactosyltransferase, β1-4galactosyltransferase, and add UDP-digalactoside (donor) to GlcNAcβ1-3Gal-saccharide (acceptor substance) mentioned above:

UDP-Galabiose+GlcNAcβ1-3Gal-R→Galα1-3Galβ1-4GlcNAcβ1-3Gal-R where R is another saccharide, as for example glucose, or an aglycon as, for example, those exemplified above. UDP-Galabiose can, for example, be synthesised with a chemical method, or an enzymatic method, from some of the enzymatically synthesised galabiose-structures (Galα1-3Gal structures) mentioned in the FIGS. 2–6.

Sequential use of β-galactosidase and α-galactosidase can, according to the invention, also be used for synthesis of, for example, Galα1-3Galβ1-4GlcNR'β-R or Galα1-3Galβ1-3GlcNR'β-R, in which R is —OH or an O-, S-, or C-glycosidically bound aliphatic or aromatic aglycon, or another type of aglycon (see A in the description), and —R' is —HAc, Teoc (trichloroethoxy-carbonyl) or another organic or inorganic group.

For example, in the first step of the synthesis use can be made of β-galactosidase, which gives Galβ1-4GlcNR'β-R (or Galβ1-3GlcNR'β-R), from for example lactose, or a mono-, di-, or tri-nitrophenyl β-galactopyranoside (or in general, in this case Galβ-R", where —R" is an aglycon selected from e.g. —F, or an aliphatic or aromatic organic group), as donor and GlcNR'β-R as acceptor. In a second synthetic step with for example α-galactosidase, Galα1-3Galβ1-4GlcNR'β-R is obtained, from for example raffinose, melibiose, or a mono-, di-, or tri-nitrophenyl α-D-galactopyranoside (or in general, Galα-R", where —R" is an aglycon selected from e.g., —F, or an organic group, which can then be e.g. an alkyl or an aromatic group), as glycosyl donor and with the lactosamine derivative, obtained in the first reaction step, as acceptor in the latter reaction.

The use of hydrophobic or charged lactosamine derivatives as acceptor can in certain cases be of value to improve the separation of product and by-products during the isolation of the trisaccharide product. In certain cases, it can be advantageous to employ more soluble derivatives of lactosamine in the α-galactosidase-reaction, in order to obtain a higher acceptor concentration (preferably higher than 0.1M) and a higher product yield. In the latter situation, an amino- or carboxyl-group containing lactosamine derivative, Galβ1-4GlcNR'β-R, can be used as acceptor in the α-galactosidase-reaction. The lactosamine derivative, obtained in the β-galactosidase-reaction, can be used directly after synthesis with β-galactosidase, or after chemical transformation.

Examples of β-galactosidase are the enzymes from *Bullera singularis* or from *Bacillus circulans* for synthesis of Galβ1-4GlcNR'β-R. Some of the α-galactosidases mentioned above, or in general, α-galactosidases which give the α1-3-linkage, are used in the preparation of the oligosaccharide.

Non-limiting examples of specific syntheses of trisaccharide derivatives are:

1. β-Galactosidase from the yeast *Bullera singularis* catalyses the following reaction:

Lactose+GlcNHTeocβ-SEt→Galβ1-4GlcNHTeocβ-SEt+Glucose

2. α-Galactosidase from coffee beans catalyses the following:

Galα-OPhNO$_2$-p+Galβ1-4GlcNHTeocβ-SEt→Galα1-3Galβ1-4GlcNHTeocβ-SEt+PNP (PNP=p-nitrophenol; GlcNHTeocβ-SEt=ethyl 2-deoxy-2-(2,2,2-trichloroethoxy-carbonylamino)-1-thio-β-D-glucopyranoside).

The synthesis above is illustrated in the non-limiting example below:

1. Galβ1-4GlcNHTeocβ-SEt.

Lactose (20 g) and acceptor (GlcNHTeocβ-SEt; NHTeoc=NH—C(=O)—O—CH$_2$—CCl$_3$; 10 g) were dissolved in 400 ml 50 mM sodium acetate, pH 6.0 and yeast cells were added (20 g). The reaction was performed at 30° C. and at pH 6.0 with slow agitation during three days. The product was purified by column chromatography (Sephadex G10; 4 liters; water as eluent), which gave unreacted acceptor (7.9 g) and product (2.8 g). NMR-data ($^{13}$C; D$_2$O-MeOD; 1:1): δ85.28 (C-1), 57.39 (C-2), 74.80 (C-3), 79.67 (C-4), 79.87 (C-5), 61.34 (C-6), 104.07 (C-1'), 72.08 (C-2'), 73.78 (C-3'); 69.67 (C-4'), 76.45 (C-5'), 62.06 (C-6'); Teoc-group: 157.03 (C=O), 75.26 (CH$_2$), 96.31(CCl$_3$).

2. Galα1-3Galβ1-4GlcNHTeocβ-SEt.

Galα-OPhNO$_2$-p (150 mg) and Galβ1-4GlcNHTeoc β-SEt (1.0 g) were dissolved in 50 mM sodium phosphate, pH 6.5, and enzyme from coffee bean (5 mg; partially purified by grinding, extraction, ammonium sulphate precipitation, dialysis, Sephadex G75 chromatography, dialysis and freeze-drying) was added. The reaction was allowed to run at room temperature, donor was added stepwise until about 300 mM nitrophenol was formed and about 10% of the acceptor had been converted to product (HPLC-analysis of the product mixture). The product was purified on Sephadex G15 (water as eluent) after extraction of p-nitrophenol at pH 4–4.5 with methylene chloride. NMR-data ($^{13}$C; D$_2$O): δ85.09 (C-1), 57.25 (C-2), 74.77 (C-3), 78.15 (C-4), 79.64 (C-5), 61.22 (C-6), 103.7 (C-1'), 70.51 (C-2'), 75.98 (C-3'), 65.75 (C-4'), 79.49 (C-5'), 61.8 (C-6'), 96.35 (C-1'), 69.10 (C-2'), 70.20 (C-3'), 70.03 (C-4'), 71.75 (C-5'), 61.91(C-6'); Teoc-group: 157.5 (C=O), 75.2 (CH$_2$), 95.81 (CCl$_3$).

In the latter reaction it is also possible, according to the invention, to simultaneously achieve preparative synthesis of Galα1-3Galα-OPhNO$_2$-p and of Galα1-3Galβ1-4GlcNHTeocβ-SEt by employing, for example, a high concentration of the reagents in the second reaction above, by, for example, using a higher concentration than 0.5 M of the two substrates. This means that two interesting products (which can be used or converted according to the invention) can be simultaneously synthesised in preparative amounts according to the latter variant of the invention. Separation of the products can be achieved using for example one or more steps (e.g. one or more of: extraction, chromatography with for example Sephadex and/or C18 silica, precipitation).

Another non-limiting example is the following:

1. β-Galactosidase from *Bullera singularis* catalyses the following:

Lactose+GlcNHTeocβ-OH→Galβ1-4GlcNHTeocβ-OH+Glucose

2. α-Galactosidase from coffee beans catalyses the following:

Galα-OPhNO$_2$-p+Galβ1-4GlcNHTeocβ-OH→Galα1-3Galβ1-4GlcNHTeocβ-OH+PNP (PNP=p-nitrophenol; GlcNHTeocβ-OH=2-deoxy-2-(2,2,2-trichloroethoxycarbonylamino)-β-D-glucopyranose).

The invention relates in this case to the above mentioned synthesis and to the above mentioned products obtained as above, or to a product derived therefrom (obtained after additional chemical or biochemical modification of the above-mentioned trisaccharide derivative), or to another similar product obtained in a corresponding manner, as well as to the use of such products, for example as a protein-, antibody-, or enzyme-inhibitor in soluble form or in immobilised form, in a clinical or diagnostic application (e.g. in the xeno-application which is mentioned in the present application). Non-limiting examples of tri-, tetra- and pentasaccharides produced (by conventional organic-chemical techniques) from the above mentioned trisaccharide derivatives (Galα1-3Galβ1-4GlcNHTeocβ-OH and Galα1-3Galβ1-4GlcNHTeocβ-SEt), are Galα1-3Galα1-4GlcNHAc, Galα1-3Galβ1-4GlcNHAcβ1-3Gal, Galα1-3Galβ1-4GlcNHAcβ1-3Galβ1-4Glc, Galα1-3Galβ1-4GlcNHAcβ-R', Galα1-3Galβ1-4GlcNHAcβ1-3Gal-R', Galα1-3Galβ1-4GlcNHAcβ1-3Galβ1-4Glc-R', Galα1-3Galβ1-4GlcNRβ-R', Galα1-3Galβ1-4GlcNRβ1-3Gal-R', Galα1-3Galβ1-4-4GlcNHRβ1-3Galβ1-4Glc -R', in which R is an organic or inorganic group as exemplified in this application, and bound to the amino group in the glucosamine part, and in which R' is an α- or β-glycosidically bound organic or inorganic group as exemplified in this application (see also the examples of A which are given in this application).

Another type of trisaccharide product are lactose derivatives, Galα1-3Galβ1-4Glc-R, of the above trisaccharides, which can be produced according to above (without β-galactosidase) from, for example, raffinose, melibiose, or a nitrophenyl α-D-galactopyranoside (or in general Galα-R", in which —R" is an aglycon, such as e.g. —F or an organic group) with lactose-R as acceptor, in which R is for example β-bound —SPhMe, —OPhOMe, —OBn or —OPhNO$_2$-p. This trisaccharide product can be used directly or be converted to the desired product with standard chemical or enzymatic method.

An additional and other type of trisaccharide derivative is Galα1-3Galα1-3Gal-R, which can be obtained according to the invention by for example (non-limiting example) a reaction between Galα-OPhNO$_2$-p as donor and Galα1-3Galα-OPhNO$_2$-p as acceptor and with α-galactosidase as catalyst.

The purification of the enzymatically produced products above is achieved by for example extraction with, for example, nitrophenol, concentration and, if possible, selective precipitation of reactant, by-product and/or product, and/or by chromatography, employing for example, one or more columns containing any of, for example, the separation materials silica, Sephadex®, Biogel, C18-silica, active carbon/Celite, ion-exchanger and, if suitable, precipitation of the product. The advantage of Sephadex or some other material with hydrophobic surfaces, is that separation of regioisomers can be achieved.

The invention relates in this case to a specific variant of the method in connection with phenyl-, methoxyphenyl, mono-, di-, or trinitrophenyl glycosides as donor in glycosidase-catalysed synthesis, that is the use of at least one of the following: one extraction step to remove phenol, methoxyphenol, or nitrophenol, after the glycosidase-catalysed reaction step, concentration and precipitation of substrate and/or of product, extraction for removal of product and substrate from the water-phase, column chromatography with Sephadex, Biogel, reversed phase silica, active carbon/Celite, ion-exchanger, and where appropriate, precipitation of the product.

The choice of α-galactosidase which gives the α1-3-regioisomer/the desired product yield, is made by the expert and does not limit the scope of the invention. Further conditions for the glycosidase-catalysed reactions above (pH, solvent, temperature, substrate concentrations—often above 0.1M concentration of acceptor, etc) are chosen by the expert and do not limit the scope of the invention.

When the trisaccharides above are formed, other trisaccharide derivatives than the α1-3-bound regioisomer are often also formed (in addition to for example hydrolysed donor), as for example the α1-6-bound regioisomer, and this and other desired regioisomers can, if desired, be hydrolysed with one or more α-galactosidases with hydrolytic specificity towards the undesired regioisomers. An alternative according to the invention is to use a 6'-modified derivative (i.e. modified in the 6-position of the galactosyl group) of Galβ1-4GlcNR'β-R or of lactose-R above, to avoid the eventual formation of the α1-6-regioisomer. A non-limiting example of such a modification is modification of the mentioned galactosyl-position with an acetyl group.

Glycosidases present in Nature, or glycosidases which have been cloned, or modified (recombinant) glycosidases which have at least about 70% correspondence with the primary amino acid sequence with glycosidases in Nature, can be used in one or more of the enzymatic reactions which have been mentioned above. This does not limit the scope of the invention, and can be of interest to achieve a higher regioselectivity, and/or a higher temperature stability, a higher operational stability, a higher activity or stability in organic solvent, a higher operational stability, and/or a higher yield (less hydrolysis). The latter can, for example, be achieved by employing an enzyme which has a higher ratio between transglycosylation reaction and hydrolysis reaction, or which has been modified specifically (by chemical or recombinant technology) in order to minimise the hydrolytic reaction. The manner of achieving this does not limit the scope of the invention and can be achieved by that e.g. at least one of the acid/base groups, which take part in the catalysis in the enzyme's active site, or some other group in the enzyme has been modified, substituted with an inert amino acid group, or has been excluded from the amino acid sequence.

The trisaccharides above can be be converted to other substances and can be used for example in the xeno-application and in the other applications according to the description.

The glycosidically bound aglycon of the above mentioned products, specified as A or R above, can be mono-, di-, tri-, oligo-, or multi(poly)functional (see for example the examples of A mentioned in this application), meaning that one, two, three or more saccharide groups are glycosidically bound to different or the same type of functional groups in A, i.e. products of for example the type (Galα1-3Galβ-)$_n$-A, (Galα1-3Galα-)$_n$-A, (Galα1-3Galβ1-4GlcNAcβ-)$_n$-A, (Galα1-3Galβ1-4GlcNAcα-)$_n$-A, (Galα1-3Galβ1-4GlcNRβ-)$_n$-A, (Galα1-3Galβ1-4GlcNRα-)$_n$-A, or (GlcNAcβ1-3Galβ-)$_n$-A, or (Galβ1-3GlcNAcβ1-3Galβ-)$_n$-A (n is an integer equal to or larger than 1) can be produced by the method according to the invention.

This can be an advantage if products with high affinity to, for example, a galabiose-binding protein or to, for example, GlcNAcβ1-3Galβ-binding bacteria are desired. The production of such products does not limit the scope of the invention, but is carried out in a straightforward manner by the expert. A in for example (GlcNAcβ1-3Galβ-)$_n$-A and (Galβ1-3GlcNAcβ1-3Galβ-)$_n$-A can be of the same types as have been mentioned above for A in the description.

As non-limiting examples, the oligosaccharide-derivatives mentioned above can be used for synthesis of bifunctional products, via e.g. coupling of the saccharide derivative with a cross-linker, such as for example DSG (disuccinimidyl glutarate) or DSS (disuccinimidyl suberate), which gives a bifunctional derivative, or with acryloyl chloride, after which the resulting conjugate can be polymerised (oligomerised) by standard methods, which gives oligofunctional products. The products can also be conjugated to, for example, a protein, such as human or bovine serum albumin, in order to produce neoglycoproteins. In the case where the oligosaccharide derivative is conjugated to acryloylchloride, one obtains for example products of the type saccharide-R—NH—C(=O)—CH=CH$_2$, which can be co-polymerised with for example acrylamide, using for example ammonium persulfate and TEMED as catalysts. The product can then be purified with for example Biogel® or Sephadex®, and moreover, if desired, can be derivatised with diethylamine or hydrazine (see for example Jakoby et al., editors, Methods Enzymology, Volume 34) in order to introduce amino groups, and the polymer can then, if desired, for example, be coupled covalently to NUNC Covalink® ELISA-plates, to NHS-activated agarose or to some of the other separation materials, which are mentioned in this descripton. These products are used analogously as other structures mentioned in this application, for analyses, separation, or inhibition. Non-limiting examples of saccharide are Galα-, Galα1-3Gal, blood group B, GalNAcα-, GalNAcα1-3Gal, GalNAcα1-3Gal51-4GlcNAc, and blood group A saccharide. Non-limiting examples of R are glycosidically bound aglycon of the type —Ph, and other aglycons mentioned above.

Manα1-6(Manα1-3)Man-R is another non-limiting example of oligosaccharide which can be used as a 'bridge' to form bi-, or oligofunctional galabiose-compounds (R is a glycosidically bound organic or inorganic group, and where R can be some of the examples of glycosidically bound R or A mentioned in this application).

In this respect, bifunctional derivatives can, as a non-limiting example, be produced by, for example, selective oxidation of the two 6-OH groups in the Manα1-6(Manα1-$^3$)-unit in the trimannoside above, to corresponding 6-C(H)=O (i.e. aldehyde groups in 6-position) which then can react with amino-group-containing aglycons in the above mentioned galabiose derivatives. The resulting Schiff bases (—N=CH—) can then be reduced to stable —NH—CH$_2$— linkages (with the help of for example sodium cyanoborohydride) between one or more-of above mentioned saccharides and Manα1-6(Manα1-3)Man-R. This procedure results in a conjugate of the type:

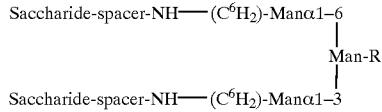

Non-limiting examples of Saccharide-spacer are one or some of Galα1-3Galα-OPh—, Galα1-3Galα-OEtPh—, Galα1-3Galβ1-4GlcNAcβ-OPh—, Galα1-3Galβ1-4GlcNAcβOEtPh—, and Galα1-3Galβ1-4GlcβOEtPh—. In this way one obtains an advantageous orientation of the galabiose units is obtained, similar to the situation in vivo. More saccharide-spacer-NH-units can be linked to the trimannoside by further oxidation of secondary hydroxyl-groups in the trimannoside. An alternative way of producing the above, is to use glycosyltransferases for modification of the trimannoside, followed by for example galactosyltransferase for bindning of for example the galabiose unit. Non-limiting examples of another type of molecule which can be used for a similar purpose, are meta-, or orto-dialdehyde, or dicarboxyl derivatives of benzene, which in a way similar to the above give a mutual orientation of the Saccharide-spacer-units relative to each other, via formation of Schiff base and subsequent reduction.

Peptide has also been mentioned above, which for example can contain one or more of serine, threonine, asparagine, lysine, glutamic acid, etc, to which the saccharide is directly glycosidically bound, or is bound via an amino- or a carboxyl-group-containing spacer.

The method according to the invention can also be used for producing products modified in one or more of the hydroxyl groups in the saccharides which have been mentioned above, (for example saccharides containing Galα1-3Gal, Galα1-3Galβ1-4GlcNAcβ- or GlcNAcβ1-3Galα-), or as modified in the Galα1-3Gal-part or GlcNAcβ1-3Galα-part of Galα1-3Galα-A, or of GlcNAcβ1-3Galβ-A, or Galβ1-3GlcNAcβ1-3Gatβ-A, respectively. This can be of interest to obtain products with modified and desired properties. Below Galα1-3Gal related products are preferentially exemplified, but the same methods can be applied to GlcNAcβ1-3Galβ-containing products.

In this way, products which have a higher affinity to a protein, for example an antibody to the Galα1-3Gal structure, or which have increased stability towards hydrolysis, or alternatively, which have increased half life in vivo, can be obtained. In this situation, e.g. an enzyme can be used. Non limiting examples are the use of lipase or protease, for example, for the acetylation of one or more of the hydroxyl groups in Galα1-3Gal-containing, or GlcNAcβ1-3Galβ-containing structures, oxidoreductase for specific oxidation of hydroxyl group(s). In this situation, an enzymatic modification technology is used which is selected by the expert, and this does not limit the scope of the invention.

Alternatively, chemical modification can be used for specific modification of one or more of the hydroxyl groups in Galα1-3Gal-containing-, or in GlcNAcβ1-3Galβ-containing structures (modified with e.g. carboxyl groups—via oxidation, or with amino groups, with other inorganic groups, with organic ester groups, with alkyl groups, or with aromatic groups), and in glucosamine-containing structures, such as Galα1-3Galβ1-4GlcNAcβ-, it can be of interest, instead of a —NHAc group, to produce and use products with another group, for example of the type R—C(O)—NH—, R—NH$_2$—, SO$_3$—NH, where R is an aliphatic, for example of the type —CH$_3$(CH$_2$)$_n$ where n is an integer in the interval 1–20, or is an aromatic group (mono-, di- or oligocyclic, example benzoyl), or is an amino acid (amide bound via its α-carboxyl or via a side-chain carboxyl group) or peptide containing group. In this situation, currently available chemical modification techniques are used and this does not limit the scope of the invention.

Glycosidically bound A can be used as spacer for linkage to another substance, for example when A contains a carboxyl group or an amino group. Examples of this are —O(CH$_2$)$_6$COOH, or —OPhNH$_2$ or —O(CH$_2$)$_2$PhNH$_2$. In this way, products suitable for, for example, column chromatography can be obtained, e.g., by coupling of Galα1-3Galβ-A or GlcNAcβ1-3Galα-A to, for example, activated agarose or cellulose. Examples of such products which are suitable for immobilisation of, for example, Galα1-3Galβ-A products, Galα1-3Galα-A products, or Galα1-3Galβ1-4GlcNAcβ-A, Galα1-3Galβ1-4Glcβ-A, GlcNAcβ1-3Galβ-A or Galβ1-3GlcNAcβ1-3Galβ-A products, obtained by the method according to the invention, are activated agarose (e.g. Sepharose® from Pharmacia), COOH-cellulose (from e.g. Whatman), material for perfusion chromatography, e.g. from Pharmacia, Perceptive and Biosepra. Microspheres, magnetic or non-magnetic, can be activated by the expert in order to immobilise the product obtained according to the invention. An example is Dynobeads® from Dyno. The expert can easily make such an immobilisation and this does not limit the scope of the invention. When A consists of a hydrophobic molecule, for example of the type O(CH$_2$)$_n$CH$_3$(n=0–18 for example), or ceramide, the product can for example be used for production of injectable liposomes.

Examples of using of soluble mono-, di-, oligo- or polyfunctional Galα1-3Gal-containing products according to the invention are in inhibition studies, inhibition in vivo of the hyperacute rejection-reaction in human beings, of, for example, xenotransplants from pig (kidney, liver, heart, for etc.) via binding to the antibodies (directed towards Galα1-3Gal) of the patient, by injection into the patient of soluble mono-, di-, oligo- or polyfunctional products according to the invention. In xenotransplantation, an initial reaction between the patient's antibodies directed to the Galα1-3Gal antigen (which is on the endothelium of the donor organ) takes place, which leads to activation of the complement system of the patient.

As non-limiting specific examples of soluble di-, and trisaccharides which can be of interest for injection and inhibition of antibodies in the xenoapplication according to the invention, and in previous parts, mention can be made of for example Galα1-3Gal, Galα1-3Galα-OMe, Galα1-3Galα-OEt, Galα1-3Galβ1-4GlcNAc, saccharide isomers, regioisomers and derivatives thereof, such as those regioisomers and derivatives thereof which can be obtained by synthesis according to the invention. Specific non-limiting examples of this concerning disaccharides and disaccharide derivatives are Galα1-2Gal, Galα-6Gal, Galα1-3Galα-OMe, Galα1-3Galα-OEt, Galα1-3Galα-O(CH$_2$)$_n$CH$_3$ (where n=an integer which is larger than or equal to zero, and preferably n=an integer in the interval 0–20), Galα1-3GalαOPhNH$_2$, Galα1-3GalαOPhNH$_2$, Galα1-3GalαOPhNHAc, Galα1-2GalαOPhNH$_2$, Galα1-6GalαOPhNH$_2$, Galα1-3GalβO(CH$_2$)$_2$PhNH$_2$, Galα1-3GalβO(CH$_2$)$_2$PhNO2, Galα1-3GalβO(CH$_2$)$_2$PhNHAc, Galα1-2GalβO(CH$_2$)$_2$PhNH$_2$, Galα1-6GalβO(CH$_2$)$_2$PhNH$_2$.

Other non-limiting examples are Galα1-3Galα-R, Galα1-3Galα-R, Galα1-2Galβ1-4GlcNAcβ-R, Galα1-6Galβ1-4GlcNAcβ-R, Galα1-3Galβ1-4GlcNAcβ-R, Galα1-3Galβ1-4GlcNR'β-R, where R' for example is of the type R"—C(O)—, or SO$_3$—, or R"—, where R"— is an aliphatic group bound to the amino group in the glucosamine residue, for example of the type CH$_3$(CH$_2$)$_n$, where n is an integer in the interval 1–20, or is an aromatic group, mono-, di- or oligocyclic, for example benzoyl, or is an amino acid (amide-bound via its α-carboxyl or via a side chain carboxyl group) or a peptide-containing group or another organic group, where R is an O-, N-, C- or S-glycosidically bound organic group, such as a group containing for example one or more of the general groups aliphatic hydrocarbon, aromatic hydrocarbon, amino group, carboxyl group, ceramide group, sulphate group, amino acid, peptide, protein, monosaccharide, disaccharide, oligosaccharide, polymer, lipid, steroid, nucloic acid, nucleotide, or R can be an inorganic group. In the case of an organic group, R can consist of for example an alkyl group, aliphatic group, aromatic group, saccharide, lipid. As non-limiting examples of Galα1-3Galα-R, Galα1-3Galα-Oceramide, Galα1-3GalαOPhNH(6-CO)-galactosyl-ceramide, Galα1-3GalαOPhNH(6'-CO)-galactosyl-ceramide, or Galα1-3GalαOPhNH(6-CO)-glucosyl-ceramide may be mentioned. As non-limiting examples of Galα1-3Galβ-R, Galα1-3Galβ-Oceramide, Galα1-3GalβOPhNH(6-CO)-galactosyl-ceramide, Galα1-3GalβOPhNH(6'-CO)-lactosyl-ceramide, or Galα1-3GalβOPhNH(6-CO)-glucosyl-ceramide may be mentioned. As non-limiting examples of Galα1-3Galβ1-4GlcNAcβ-R, Galα1-3Galβ1-4GlcNAcβ-Oceramide, Galα1-3Galβ1-4GlcNAcβ-OPhNH(6-CO)-galactosyl-ceramide, Galα1-3Galβ1-4GlcNAcβ-OPhNH(6'-CO)-lactosyl-ceramide, or Galα1-3Galβ1-4GlcNAcβ-OPhNH(6-CO)-glucosyl-ceramide, amino acid, peptide, protein or a group from more than one of these groups, may be mentioned. Examples of alkyl groups are groups of the type —(CH$_2$)$_n$CH$_3$, where n=an integer which is larger than or equal to zero, and preferably n=an integer in the interval 0–20. Non-limiting examples in the case R=saccharides are: N-acetyl-glucopyranosyl group (GlcNAc-group), for example bound via the 4-position in GlcNAc, or a similar bound GlcNAc-group in which instead of a —NHAc group, another group is used, for example of the type R—C(O)—NH—, R—NH$_2$—, SO$_3$—NH, where R is an aliphatic group, for example of the type CH$_3$(CH$_2$)$_n$, where n is an integer in the interval 1–20, or where R is an aromatic group, mono-, di- or oligocyclic, for example benzoyl, or is an amino acid (amide-bound via its α-carboxyl group or via a side-chain carboxyl group) or where R is a peptide-containing group), a glucopyranosyl group (Glc-group), another monosaccharide, a disaccharide containing any of these or a derivative thereof, an oligosaccharide containing one or more of these groups or a derivative thereof, a polymer based on e.g. a peptide chain, such as polylysine or a polymer containing one or more of the amino acids asparagine, glutaminic acid, serine, threonine, glycine, etc, an oligosaccharide for example of the types which have been mentioned above, polysaccharide such as agarose or cellulose, polystyrene, polyacrylamide, polyvinylalcohol, polyethylene glycol (see e.g. Shearwater polymers' catalogue with non-limiting examples of polyethylene glykol derivatives, which can be used—according to the invention—for production of mono-, di-, or multi-functional products,—in the latter case, for example of the type tresyl-Star-PEG, in which the carbohydrate can be bound, for example via an amino group containing spacer bound as aglycon to the sugar), etc. Examples of amino acids are asparagine, serine, threonine, etc.

Other specific non-limiting examples according to the invention concerning trisaccharides and trisaccharide derivatives for injection are Galα1-2Galβ1-iGlcNAc, Galα1-6Galβ1-iGlcNAc, Galα1-3Galβ1-iGlcNAc, Galα1-2Galβ1-iGlcNAcβOPhNH$_2$, Galα1-6Galβ1-iGlcNAcβOPhNH$_2$ Galα1-3Galβ1-iGlcNAcβO(CH$_2$)$_2$PhNH$_2$, Galα1-2Galβ1-iGlcNAcβO(CH$_2$)$_2$PhNH$_2$, Galα1-6Galβ1-iGlcNAcβOPhN H$_2$, Galα1-3Galβ1-iGlcNAcβOPhNH$_2$, Galα1-2Galβ1-iGlcNAcβOPhNH$_2$, Galα1-6Galβ1-iGlcNAcβOPhNH$_2$, (in which i represents one of the integers 3, 4, or 6), Galα1-2GalβB-iGlcNR, Galα1-6Galβ1-iGlcNR, Galα1-3Galβ1-iGlcNR, Galα1-2Galβ1-iGlcNRβOPhNH$_2$, Galα1-6Galβ1-iGlcNRβOPhNH$_2$, Galα1-3Galβ1-iGlcNRβO(CH$_2$)$_2$PhNH$_2$, Galα1-2Galβ1-iGlcNRβO(CH$_2$)$_2$PhNH$_2$, Galα1-6Galβ1-iGlcNRβOPhNH$_2$, Galα1-3Galβ1-iGlcNRβOPhNH$_2$, Galα1-2Galβ1-iGlcNRβOPhNH$_2$, Galα1-6Galβ1-iGlcNRβOPhNH$_2$, (in which i represents one of the integers 3, 4, or 6, and in which R is an inorganic or organic aliphatic or aromatic group, e.g. as exemplified on the preceding page, bound to the amino group on the glucose-amino group, i.e. for example where instead of a —NHAc group another group is used, for example of the type R—C(O)—NH—, R—NH—, SO$_3$—NH, where R is an aliphatic group, for example of the type CH$_3$(CH$_2$)$_n$, where n is an integer in the interval 1–20, or is an aromatic group, mono-, di- or oligocyclic, for example benzoyl, or is an amino acid (amide-bound via its α-carboxyl or via a side-chain carboxyl group) or a peptide-containing group.

The amino groups in the aglycon groups in the specific examples above can be modified with. for example a mono-, di-, tri-, or oligofunctional organic or inorganic group, i.e. in general saccharide-aglycon-NHCO—R, of which as non-limiting examples of CO—R, mention can be made of: (6',6"CO)-modified trimannoside (which has been mentioned above), other CO-modified oligosaccharide, lipid for example 6-CO-galactosyl-ceramide or 6'-CO-lactosyl-ceramide, or 6-CO-glucosylceramide as non-limiting examples, CO—(CH$_2$)$_n$CH$_3$ group (n is an integer in for example the interval 1–20), such as stearyl, butyryl, propionyl, acetyl (in the latter case in for example Galα1-3GalαOPhNHAc, Galα1-3Galβ1-3GlcNAcβOPhNHAc, Galα1-3Galβ1-3GlcNAcβO(CH$_2$)$_2$PhNHAc, and in Galα1-3Galβ1-4GlcNAcβO(CH$_2$)$_2$PhNHAc), an amino acid or amino acid derivative, a cross-linker, e.g. of the type —CO—(CH$_2$)$_n$—CO— (i.e. the di- or trisaccharide derivative is bivalently bound together with a cross-linker; n is an integer, preferably in the range 0–18), —CO—(CH$_2$)$_n$—COOH (i.e. this type of derivative ends with a carboxyl group; n is an integer preferrably in the range 0–18), —CO—(CH$_2$)$_n$—NH$_2$ (i.e. this type of derivative ends with an amino group; n is an integer, preferrably in the range 0–18). The amino groups mentioned here can also be modified with one or more of the other di-, oligo-, or polyfunctional reagents which have been mentioned above, see above examples of PEG, oligosaccharides, peptides, and thereby di-, oligo- or polyfunctional soluble trisaccharide derivatives can be obtained (cf. the description concerning for example A above).

Non-limiting examples of soluble tetrasaccharides and pentasaccharides which can be of interest for the xenoapplication is e.g. Galα1-3Galβ1-4GlcNAcβ1-3Gal, Galα1-3Galβ1-4GlcNAcβ1-3Galβ1-4Glc, Galα1-3Galβ1-4GlcNRβ1-3Gal, Galα1-3Galβ1-4GlcNRβ'1'-3Galβ1-4Glc, regioisomers and derivatives thereof, such as the regioisomers, analogues and mono-, di-, oligo- or polyfunctional derivatives which can be obtained by the synthetic method according to the invention and which have been described above. Other non-limiting examples are analogous tetra- and pentasaccharide structures as above, but which contain Galα1-2Galβ1-iGlcNR, Galα1-6Galβ1-iGlcNR, Galα1-3Galβ1-iGlcNR (where R is bound to N in glucosamine; R has been exemplified above) and structures which, for example, contain the aglycons which have been described above.

According to the invention, additional examples of compounds for injection are saccharide glycosides and derivatives as above which contain at least one reactive group, e.g. in the aglycon part or bound via the amino group on the glucosamine part of, for example, a trisaccharide of the type Galα1-3Galβ1-4GlcNR. This reactive group can be used according to the invention to react with e.g. xeno-reactive antibodies. Specificity is obtained due to the fact that the carbohydrate part binds to the antibody and this facilitates the reactive group preferably reacting with groups close to the specific binding site of the antibody, causing a strong inhibition of the antibody's antigen-binding ability. The literature is extensive on this type of so-called affinity-labelling as well as on reactive groups in connection therewith, and this does not limit the scope of the invention.

The galabiose-antibodies that are to be inhibited in the plasma of the patient e.g. in xenotransplantation, are of a heterogeneous nature; some bind relatively strongly and specifically to galabiose, other antibodies bind in a relatively weaker manner to the galabiose structures and better to trisaccharides and trisaccharide derivatives. According to the present invention, a mixture of galabiose-containing di-, tri-, or higher oligosaccharides or glycosides thereof can be useful to inject, e.g. because the less complex disaccharide and/or disaccharide derivative can be used to inhibit a substantial part of the galabiose- antibodies in the blood of the patient, and the injected ,trisaccharide and/or trisaccharide derivative can be used for inhibition of the antibodies in the blood of the patient, which preferably bind to trisaccharide and/or trisaccharide derivatives.

The same applies to the stereo- and regioisomers, e.g. some of the antibodies in the plasma of the patient which have specificity towards stereoisomeric digalactosides of the type Galα1-3Galα- and other antibodies specific to regioisomers, such as Galα1-6Gal and Galα1-3Galβ1-3GlcNAc. These antibodies in the plasma of the patient can bind to di- and trisaccharide structures present on a transplanted pig organ and cause an acute rejection response. According to the invention, a mixture, not only of di- and trisaccharide(derivative), but also of stereo- and/or of regioisomers can therefore be injected in the blood of the patient to inhibit the rejection reaction of a pig organ transplanted to a human.

As a non-limiting example of a mixture of regioisomers which can be of interest for use in the xenoapplication, mention can be made of a 3/2 mixture of the two trisaccharide derivatives Galα1-3Galβ1-4GlcNAcβO(CH$_2$)$_2$PhNHAc and Galα1-3Galβ1-3GlcNAcβO(CH$_2$)$_2$PhNHAc which have been shown to considerably decrease the binding of human antibodies (from pooled plasma and from blood group O plasma) to pig cells and also inhibits the subsequent lysis of the cells (at a total concentration of the trisaccharide-derivative mixture in the interval 2.5 mg to 0.1 mg per milliliter human plasma).

Such a mixture of trisaccharide regioisomers can be obtained according to the invention after, for example, chemical synthesis with for example Galα1-3GalβSPh as donor and with 6-BenzoylGlcNAcβO(CH$_2$)$_2$PhNO$_2$-p as acceptor followed by conventional chemical modification (see the description for further information on the synthesis). As non-limiting examples of disaccharide and trisaccharide mixture for injection mention can be made of injection of one or more of the below mentioned mixtures: Galα1-3Galβ1-4GlcNAcβO(CH$_2$)$_2$PhNHAc and Galα1-3Galα-OMe or Galα1-3Galβ1-4GlcNAcβO(CH$_2$)$_2$PhNHAc and Galα1-3Galα-OEt or Galα1-3Galβ1-4GlcPO(CH$_2$)$_2$PhNHAc and Galα1-3Galα-OPhNH$_2$-p or Galα1-3Galβ1-4GlcNAcβOR and Galα1-3Galα-OR' or (Galα1-3Galβ1-4GlcNAcβ)$_n$-A and (Galα1-3Galα)$_n$-A', where A, A', R and R' are chosen from some of the above mentioned examples of mono-, di-, oligo-, or polyfunctional A or R, and where n is an integer for example=1, or 2 (bifunctional saccharide), or n is for example in the interval 3–10, and Galα1-3Galβ1-4GlcβO(CH$_2$)$_2$PhNHAc and Galα1-3Galα-OMe or Galα1-3Galβ1-4GlcβO(CH$_2$)$_2$PhNHAc and Galα1-3Galα-OEt or Galα1-3Galβ1-4GlcβO(CH$_2$)$_2$PhNHAc and Galα1-3Galα-OPhNH$_2$-p or Galα1-3Galβ1-4GlcβOR and Galβ1-3Galα-OR' or (Galα1-3Galβ1-4Glcβ)$_n$-A and (Galα1-3Galα)$_n$-A', where A, A', R and R' are chosen from some of the above mentioned examples of mono-, di-, oligo-, or polyfunctional A or R and where n is an integer for example=1, or 2 (bifunctional saccharide), or n is for example in the interval 3–10, and Galα1-3Galβ1-4GlcNAcβOPhNH$_2$ and Galα1-3Galα-OMe or Galα1-3Galβ1-4GlcNAcβOPhNH$_2$ and Galα1-3Galα-OEt or Galα1-3Galβ1-4GlcNAcβOPhNH$_2$ and Galα1-3Galα-OPhNH$_2$-p and Galα1-3Galβ1-4GlcNAcβOPhNHR and Galα1-3Galα-OMe or Galα1-3Galβ1-4GlcNAcβOPhNHR and Galα1-3Galα-OEt or Galα1-3Galβ1-4GlcNAcβOPhNHR and Galα1-3Galα-OPhNH$_2$-p or Galα1-3Galβ1-4GlcNAcβR and Galα1-3Galα-R' or (Galα1-3Galβ1-4GlcNAcβ)$_n$-A and (Galα1-3Galα)$_n$-A', where A, A', R and R' are chosen from some of the above mentioned examples of mono-, di-, oligo-, or polyfunctional A or R. and where n is an integer for example=1, or 2 (bifunctional saccharide), or n is for example in the interval 3–10, and Galα1-3Galβ1-4GlcNRβOPhNH$_2$ and Galα1-3Galα-OMe or Galα1-3Galβ1-4GlcNRβOPhNH$_2$ and Galα1-3Galα-OEt or Galα1-3Galβ1-4GlcNRβOPhNH$_2$ and Galα1-3Galβ-OPhNH$_2$-p or (Galα1-3Galβ1-4GlcNRβOPhNH-)$_n$-A and (Galα1-3Galα)$_n$-A', where A, A', R, R' and R" are chosen from some of the above mentioned examples of mono-, di-, oligo-, or polyfunctional A or R. and where n is an integer for example=1, or 2 (bifunctional saccharide), or n is for example in the interval 3–10, and Galα1-3Galβ1-4GlcNRβOPhNHR' and Galα1-3Galα-OMe or Galα1-3Galβ1-4GlcNRβOPhNHR' and Galα1-3Galα-OEt or Galα1-3Galβ1-4GlcNRβOPhNHR' and Galα1-3Galα-OPhNH$_2$-p or Galα1-3Galβ1-4GlcNRβ-R' and Galα1-3Galα-R" or (Galα1-3Galβ1-4GlcNRβ)$_n$-A and (Galα1-3Galα)$_n$-A', where A, A', R, R' and R" are chosen from some of the above mentioned examples of mono-, di-, oligo-, or polyfunctional A or R, and where n is an integer for example=1, or 2 (bifunctional saccharide), or n is for example in the interval 3–10.

The above mentioned examples of mixtures av di-, tri-, tetra-, and/or pentasaccharide glycosides are also of interest for coupling to separation material for use in an affinity column (affinity chromatography) for the purification, or for the removal of, for example, antibodies from the plasma of patients before and/or after a transplantation of, for example, a pig organ to a patient.

Such an affinity column can, for example, contain a mixture of, for example, the above mentioned types of saccharides which have been immobilised via a spacer to a separation material, or different immobilised saccharides can be used in separate columns which can be used in series.

When used in connection with xenotransplantation, the use of products according to the invention is not limited to the use of organs present in Nature. In order to minimise the rejection reaction in connection with xenotransplantation, it is useful according to the invention to inject the patient with a combination of soluble mono-, di-, oligo- or polyfunctional products according to the invention in connection with and after xenotransplantation of so-called transgenic organs obtained from recombinant (transgenic) pigs. In such organs the expression of for example the Galα1-3Gal epitope has been reduced (employing for example the introduction of the Gal α(1-2)fucosyltransferase gene for expression of Galα (1-2)fucosyltransferase, which gives synthesis of the blood-group H epitope which does not cause rejection), and/or the organs have been equipped with genes for expression of e.g. protein(s) with the ability to inhibit that part of the patient's rejection reaction which is mediated by his or hers complement system. Examples hereof are genes for expression of CD59 and so-called decay accelerating factor. Examples of references of the above types of transgenic organs/cells from pig are described in Nature Medicine, volume 1, pages 1248–1250 and pages 1261–1267.

The amount of injected soluble products in the applications above is often decided by the expert for every single product and does not limit the scope of the invention. Examples of relevant amounts of injected substance per litre of plasma are from 5 mg, or from 10 mg, or from 20 mg, or from 40 mg, or from 100 mg to 10 g, or to 5 g, or to 2 g, or to 1 g, or to 0.5 g, or to 0.2 g. The higher amount applies to e.g. non-toxic products, or to products of lower activity per unit, while the lower amount applies to e.g. products which have higher activity.

Examples of the use of soluble mono-, di-, oligo-, or polyfunctional GlcNAcβ1-3Galβ-containing products or Galβ1-3GlcNAcβ1-3Galβ-containing products according to the invention are for inhibition studies, for inhibition in vivo of for example infections in the respiratory tract.

An example of using non-soluble Galα1-3Gal-containing products produced according to the invention, is to use them e.g. as separation products for separation from the plasma of the patient of a large part of the above mentioned antibodies, so that it is possible to minimise the rejection reaction in, for example, xenotransplantation of natural existing organs or in xenotransplantation of organs from recombinant animals according to, for example, the non-limiting examples above.

Non-limiting examples of such non-soluble separation products obtained according to the invention are Galα1-3Galβ-A covalently bound to agarose (e.g. after reaction between Galα1-3Galβ-A and tresyl-activated agarose or N-hydroxysuccinimide-activated carboxyl-agarose or carboxyl-cellulose), or covalently bound to other materials, such as for cellulose. A contains a spacer; non-limiting examples of this are —O(CH$_2$)$_6$NH$_2$, or as a preferred type of spacer according to the invention, —OPhNH$_2$ with a reactive group for covalent coupling, see above. The choice of spacer, activated agarose, or cellulose and the production of covalent bound products can simply be made by the expert and do not limit the scope of the invention. Examples of distributors of agarose, cellulose and other suitable separation materials are Sepharose® from Pharmacia (cross-linked, CL, or not cross-linked), COOH— cellulose (from e.g. Whatman), material for perfusion chromatography, e.g. from Pharmacia, Perceptive Biosystems and Biosepra. More specific non-limiting examples of separation products produced and used according to the invention based on agarose or cellulose are Galα1-3Galα-O(CH$_2$)$_2$PhNHCO--Sepharose®, Galα1-3Galα-O(CH$_2$)$_2$PhNHCO--Cellulose, Galα1-3Galα-OPhNHCO--Sepharose®, Galα1-3Galα-OPhNHCO--Cellulose, Galα1-3Galβ1-4GlcNAcβ-OPhNHCO--Sepharose® and Galα1-3Galβ1-4GlcNAcβ-OPhNHCO--Cellulose. Galα1-3Galβ1-4GlcNAcβ1-3GalβOPhNHCO--Sepharose® and Galα1-3Galβ1-4GlcNAcβ1-3GalβOPhNHCO--Cellulose. Galα1-3Galβ1-4GlcNAcβ-O(CH$_2$)$_2$PhNHCO--Sepharose® and Galα1-3Galβ1-4GlcNAcβ-O(CH$_2$)$_2$PhNHCO--Cellulose. Galα1-3Galβ1-4GlcNAcβ1-3Galβ1-4GlcβOPhNHCO--Sepharose® and Galα1-3Galβ1-4GlcNAcβ1-3Galβ1-4GlcβOPhNHCO--Cellulose. Galα1-3Galβ1-4GlcNAcβ1-3GalβO(CH$_2$)$_2$PhNHCO--Sepharose® and Galα1-3Galβ1-4GlcNAcβ1-3GalβO(CH$_2$)$_2$PhNHCO--Cellulose. Galα1-3Galβ1-4GlcNAcβ1-3Galβ1-4GlcβO(CH$_2$)$_2$PhNHCO--Sepharose® and Galα1-3Galβ1-4GlcNAcβ1-3Galβ1-4GlcβO(CH$_2$)$_2$PhNHCO--Cellulose. GlcNAcβ-O(CH$_2$)$_2$PhNHCO--Sepharose® and GlcNAcβ-O(CH$_2$)$_2$PhNHCO--Cellulose. GlcNAcβ1-3GalβO(CH$_2$)$_2$PhNHCO--Sepharose® and GlcNAcβ1-3GalβO(CH$_2$)$_2$PhNHCO--Cellulose. Galβ1-3GlcNAcβ1-3GalβO(CH$_2$)$_2$PhNHCO--Sepharose® and Galβ1-3GlcNAcβ1-3GalβO(CH$_2$)$_2$PhNHCO--Cellulose. Galβ1-3GlcNAcβ1-3Galβ1-4GlcβO(CH$_2$)$_2$PhNHCO--Sepharose® and Galβ1-3GlcNAcβ1-3Galβ1-4GlcβO(CH$_2$)$_2$PhNHCO--Cellulose.

CO--Cellulose or CO--Sepharose (agarose), or CO-Cellulose or CO-Sepharose, means that cellulose or Sepharose has been modified with a carboxyl group containing substance, which then is activated in the carboxyl group with e.g. N-hydroxysuccinimide and is used for coupling of the carbohydrate substances above.

Non-limiting examples of commercially available agarose material, to which saccharide-containing ligands can be coupled according to the invention, are material of the type CM-Sepharose® Fast Flow and NHS-activated Sepharose® Fast Flow.

The latter is used in a preferred variant of the invention in the products which are mentioned above. The latter material or support (NHS-activated Sepharose-FF®; e.g. available from Pharmacia) can be used directly for coupling (i.e. without preceding activation) of amino group containing saccharides according to the invention. A preferred variant of the invention is given as a non-limiting example below: It is reacted, under sterile conditions, n g of saccharide-spacer (e.g. Galα1-3Galα-OPhNH$_2$ or Galα1-3Galβ1-4GlcNAcβ-OPhNH$_2$; where n is, for example, an integer or another number in the interval 1–20, and typical non-limiting examples are n=either of 5, 8, 10, 12, 15 or 20) per kg gel weight of NHS-activated Sepharose-FF® at pH 7.5 or pH 8.0, in a non-limiting typical example, in buffer (for example 0.1 M sodium phosphate as non-limiting example), during 2 hours or during 20 hours and in the example at room temperature. The material is washed on a glass-filter or under other sterile conditions with buffer and is treated with, for example, Tris-HCl buffer in order to react the remaining reactive groups.

The CM-variant can also be used but requires preceding activation.

Instead of cellulose or agarose, other support materials can be used, which have been mentioned above e.g. POROS® 20, POROS® 50 which are activated e.g. with epoxy groups or by another activation method, for coupling of above mentioned ligands.

Also a combination of two or more immobilised carbohydrates on one and the same support, or a mixture of two or more of the above mentioned supports, can be used, packed in one column or in two separate columns (where the columns can contain the same or different amounts of immobilised saccharide), for separation from blood of e.g. antibodies against the Galα1-3Gal-epitope. Non-limiting examples of this are immobilisation of the disaccharide derivatives Galα1-3Galα-OPhNH$_2$ and Galα1-3Galβ1-4GlcNAcβ-O(CH$_2$)$_2$PhNH$_2$ on for example DSC-activated (activated with Di-N-succimidyl carbonate) COOH-Sepharose or COOH-Cellulose, or immobilisation on e.g. POROS® 50 activated e.g. with epoxy groups or by another activation method.

Also monosaccharide-derivatives of the type Galα-spacer, where spacer symbolises an O-, S- or C-glycosidically bound organic molecule suitable for covalent binding to a separation material, can be of interest to bind to the separation material of above mentioned type for removal of a part of or a majority of antibodies against Galα1-3Gal-epitope. Non-limiting examples of such separation material are Galα-OPhNHCO--Sepharose® and Galα-O(CH$_2$)$_2$PhNHCO--Sepharose®.

Examples of advantages of such combinations of different mono-, di-, tri- and or higher saccharides immobilised in one or in different columns, are that it is possible to use e.g. the immobilised mono- and/or disaccharide ligand for removal (e.g. from a patient's blood) of the majority of the antibodies, and the immobilised trisaccharide ligand and/or an immobilised higher oligosaccharide can be used (in a smaller amount than had been the case if the higher oligosaccharide had been used alone) for removal of the remaining antibodies (e.g. antibodies with lower binding ability towards the disaccharide ligand than towards the trisaccharide ligand and/or towards the higher oligosaccharide ligand). In this way two purposes can be achieved: on one hand a more complete removal of the antibodies in question and on the other hand a minimisation of the use of trisaccharide ligands or higher oligosaccharide ligands, which are considerably more expensive to produce (also according to the present invention) than the disaccharide ligands.

As mentioned above, di-, tri-o oligo- or multimeric saccharide ligands can also be produced and be immobilised to separation materials (for example of above mentioned type) for removal of antibodies towards Galα1-3Gal-epitope. In this way, a higher affinity between antibody and separation material may be achieved. This can in turn make it possible to achieve a more complete removal of antibodies (especially of such antibodies as have specificity, but have a lower affinity to the monofunctional, di-, tri-, or higher oligosaccharide ligands, when compared with other antibodies towards the Galα1-3Gal-epitope). A non-limiting example of such oligomeric ligands is human serum albumin (HSA) conjugated with, for example, Galα1-3Galα-OPhNH$_2$ and/or with Galα1-3Galβ1-4GalcNAcβ-OPhNH$_2$, and/or with Galα1-3Galβ1-4GlcNAcβ-O(CH$_2$)$_2$PhNH$_2$ used as a non-limiting example. employing for example a carbodiimide reaction for the conjugation reaction, or a cross-linker, for example of the type BS (bis-sulfo-succinimidyl suberate) to prepare the conjugate. This non-limiting example with conjugate of the type (Galα1-3Galα-OPhNH-CO)n-HSA and/or Galα1-3Galβ1-4GlcNAcβ-O(CH$_2$)$_2$PhNH-CO)n-HSA and/or Galα1-3Galβ1-4GlcNAcβ-OPhNH-CO)n-HSA, can be immobilised, for example, in the same manner to the separation materials (supports) which have been mentioned above. The resulting material can be used for removal of antibodies towards the Galα1-3Gal-epitope. This type of separation material based on immobilised di-, tri-, oligo-, or multimeric saccharide ligands can be used alone for removal of antibodies towards the Galα1-3Gal-epitope, or can be used in combination with the separation materials which have been mentioned above (containing the above mentioned types of immobilised mono-, di-, tri-, and/or higher oligosaccharide ligand).

As has been mentioned above, CO--Cellulose or CO--Sepharose (agarose), or CO-Cellulose or CO-Sepharose, means that cellulose or Sepharose (agarose) has been modified with a carboxyl-group-containing substance, which has then been activated in the carboxyl groups, with e.g. N-hydroxysuccinimide or DSC, and has been used for coupling of the carbohydrate substances above. Non-limiting examples of Sepharose for immobilisation have been mentioned above. Instead of cellulose or agarose other materials can be used, which have been mentioned above, e.g. POROS® 50 activated e.g. with epoxy groups or by some other activation method, for coupling of above mentioned saccharide ligands.

The separation products which have been mentioned above can also be used for purification of enzymes or cells, bacteria, toxins, antibodies and other proteines which have been mentioned in the introduction above. If, in the examples which have been given above, the structures which are coupled to Sepharose, cellulose or POROS material instead have been coupled to activated microtiter wells in ELISA-plates (e.g. as obtained from NUNC, Denmark), products are obtained which are suitable for ELISA-determination of enzyme cells, bacteria, proteins, antibodies, cells in a test, which has been mentioned in the introduction above.

Non-limiting examples of coupling to NUNC Covalink are the adding of BS (bis-sulfo-succinimidyl suberate) to NUNC Covalink and then adding some of the saccharides mentioned above or other saccharide ligands. Non-limiting examples are the adding of either Gal$\alpha$1-3Gal$\alpha$-OPhNH$_2$, or Gal$\alpha$1-3Gal$\beta$1-4GlcNAc$\beta$-O(CH$_2$)$_2$PhNH$_2$ (for determination of antibody towards the Gal$\alpha$1-3Gal epitope), or Gal$\alpha$1-3(Fuc$\alpha$1-2)Gal$\beta$-O(CH$_2$)$_2$PhNH$_2$-p (for determination of the blood group B determinant). The remaining active groups can then be blocked or can be reacted with e.g. Tris-HCl or an inert protein, for example HSA.

The determination of the component in the sample, e.g. antibodies towards the Gal-Gal-epitope, or towards the B determinant in the above example, is carried out by, as a non-limiting example, and after washing (according to, for example, the recommendations by NUNC) of the wells on the plate derivatised with saccharide according to that stated above: adding the sample to the wells, incubate, wash with for example the recommended buffer, add enzyme-protein conjugate (for example peroxidase conjugated with antibody specific towards human antibody), incubating, washing the wells and adding substrate (e.g. OPD-tablets as substrate for peroxidase in ELISA, as recommended by for example DakoPatts in Denmark), incubating and finally measuring the absorbance in the wells. The method above is a non-limiting example and the determination of the component in the sample can be done in several different ways, which are easily determined by the expert and this does not limit the scope of the invention. For example, instead of the sandwich method above, use can be made of a competitive or non-competitive method and also many different types of conjugates and substrates for the detection, including e.g. a biotin-avidin system for increase of the sensitivity, or of protein A conjugate or other conjugates, which are chosen by the expert for the specific application.

The above mentioned method can also be used in general for coupling of other saccharide ligands containing an amino-group (e.g. of the type OPhNH$_2$ or O(CH$_2$)$_2$PhNH$_2$) to NUNC Covalink®. Non-limiting examples of this are coupling of the blood group A determinant with spacer (for example GalNAc$\alpha$1-3(Fuc$\alpha$1-2)Gal$\beta$-O(CH$_2$)$_2$PhNH$_2$-p) in the same way as described above for the determination of antibodies towards the blood group A determinant, and the coupling, in the same way as above, of saccharide ligands which are acceptors for the glykosyltransferases, of saccharide ligands which bind to lectins, selecting, adhesins, enzymes, or toxins, for determination in the same way as above of glycosyltransferases, lectins, selecting, adhesins, enzymes, toxins, bacteria, virus or cells in a sample. The literature is extensive concerning the description of the specificity of different saccharides towards different glycosyltransferases, lectins, selecting, adhesins, enzymes, toxins, bacteria, or virus and these are chosen by the expert for the specific application. This method in its broader application thus facilitates determination of a broad spectrum of different components.

The carbohydrate structures which are mentioned in this application can also be used for covalent conjugation to the enzymes which can be used in ELISA, and the resulting conjugate can be used for determination of proteins exemplified above, or for determination of soluble carbohydrate. Examples of the latter are conjugation of peroxidase (which first has been oxidised with periodate), with for example Gal$\alpha$1-3Gal$\beta$-OPhNH$_2$-p, or with Gal$\alpha$1-3Gal$\beta$1-4GlcNAc$\beta$-OPhNH$_2$-p, followed by reduction with sodium cyanoborohydride, followed by chromatography (purification of the conjugate) with for example Sephadex G50 or Sephadex G75. This conjugate can then be used, as a non-limiting example, for the determination of Gal$\alpha$1-3Gal$\beta$ or Gal$\alpha$1-3Gal$\beta$1-4GlcNAc$\beta$-saccharides, via for example step 1: Adsorption of antibodies with specificity towards any of the above structures on a mikrotiter plate,
2: Application of a sample containing any of the above saccharides to the microtiter wells together with peroxidase conjugate, followed by
3: Application of peroxidase substrate and measurement of the absorbance in the wells. In this method one obtains an absorption which is decreasing when the soluble carbohydrate concentration is increasing. Instead of this competitive assay, many other configurations can be used. For determination of proteins or antibodies against, for example, the above galabiose-structures, the plate can first be incubated with anti-human antibody, followed by incubation with antibody specific to galabiose, subsequently peroxidase-galabiose conjugate, subsequently substrate, and finally measurement of absorbance. Incubation times, buffers and washing between every step correspond to standard conditions, or are modified as will be easily determined by the expert. In a similar way, many other types of enzymes which are used in ELISA, can be conjugated with the carbohydrates according to the invention, and the resulting conjugates can be used correspondingly. In a similar way, the carbohydrates can be conjugated to, for example, biotin and the conjugate can be used together with streptavidin-enzyme conjugate in, for example, a competitive assay of soluble carbohydrate, or for the determination of protein or antibody against for example galabiose.

In the affinity application in the xenotransplantation examples given above, the separation product can, according to the invention, be packed in one column or in different columns, and plasma from the patient is passed through the mentioned column(s) for specific removal of the patient's antibodies against Gal$\alpha$1-3Gal. Alternatively, the product can be in the form of magnetic microspheres (for example Galα1-3Gal covalently bound via a spacer—for example of the above mentioned types—to for example tosyl-activated Dynobeads®), which will be added to the plasma of the patient, upon which the patient's antibodies towards Galα1-3Gal are bound to the microspheres and are separated by removal of the microspheres with the aid of a magnet.

After treatment with the column(s) and/or magnetic particles, the rejection response can be further minimised, according to the invention, by injection of a saccharide, or a saccharide derivative, or two or more different soluble mono-, di-, oligo-, and/or polyfunctional products according to the invention.

The design of the column, the system of the column(s), regeneration (elution of bound antibody) from the column, and the amount of the separation material and of the soluble carbohydrate products (for example the concentrations of soluble products for injection, see above) are determined by the expert and do not limit the scope of the invention. Non-limiting examples of the diameter of the separation material in the column can for example be from 5 mm, or from 10 mm, or from 20 mm, or from 40 mm, to 200 mm, or to 150 mm or to 100 mm and the packed height of the separation product in the column can be for example from 25 mm, or from 50 mm, or from 75 mm, or from 100 mm, to 500 mm, or to 400 mm or to 200 mm, or according to the dimensions which are used today for protein-A columns. One column can be used, or two, or three or more columns can be used in series to get an optimal removal of antibody from the blood or plasma of the patient.

Alternatively, the treatment can be carried out by, for example, allowing plasma from the patient to pass a column, or columns, with a Galα1-3Gal-containing product, or products, before the passage of the plasma through a naturally existing or recombinant organ, (e.g. kidney or liver) from, for example, pig, connected outside the patient, in this way minimising the rejection reaction of the plasma of the patient towards for example a pig kidney or a pig liver. Before the contact with the pig organ and after treatment with column or magnetic particles, it is possible to obtain, according to the invention, a further minimisation of the rejection reaction by addition of soluble mono-, di-, oligo-, and/or polyfunctional product(s) according to the invention.

What has been mentioned above for the xenotransplantation application of saccharides can, according to the inventions also be applied to the case of donation of an organ from a human donor to a patient of blood group B or A, in which case blood group A saccharides or blood group B saccharides and/or immobilised derivatives thereof, are used in, for example, a manner corresponding to that mentioned above for the xeno case.

As has been mentioned above for the xenotransplantation application, the application of soluble and/or immobilised saccharides can be used with transgenic or with non-transgenic organs and in combination with another treatment which can be of interest (immunosuppressors, etc). A non-limiting example is treatment including treatment with α-galactosidase which has been covalently modified with organic groups. A non-limiting example of this is PEG-conjugated enzyme (PEG-derivatives for conjugation have been exemplified above) in order to minimise the immunogenicity and prolong the half-life of the enzyme. This PEG-enzyme can be used to minimise the number of Galα1-3Gal-epitopes on the pig organ (specific hydrolysis of the Galα-linkage) before and after the transplantation in order to minimise the antibody reaction.

The production of PEG-conjugated α-galactosidase (a non-limiting example of enzyme source is coffee beans from which the enzyme can be purified according to the principles described above) does not limit the scope of the invention but is carried out by the expert by applying known technology for PEG-conjugation of proteins. Below follow additional, non-limiting examples of the practical use of the invention.

1. Synthesis of GlcNAcβ-O(CH$_2$)$_5$COOEt

GlcNAcβ-PNP (70 g) and HO(CH$_2$)$_5$COOEt (32 g) were mixed in 2.2 liter 50 mM sodium acetate buffer, pH 6.0, and 17 g of N-acetyl-β-D-glucosaminidase preparation from *Aspergillus oryzae* was added at room temperature. The reaction mixture was agitated, and stopped after 10 hours with heat treatment (5 min. at 80° C.). The mixture was centrifuged 30 min at 11300 g (removed most of the non-reacted donor substrate, about 38 g) and the water-phase was extracted with etyl acetate in order to remove unreacted ester substrate and p-nitrophenol. The water phase was concentrated and applied on Sephadex G10 (about 20 liter bed volume). Elution with water gave a product mixture (about 25 g) which was purified by chromatography on silica (CMH/7:4:0.3). This gave 15 g product (about 45% w/w calculated on reacted donor), which was pure according to NMR. NMR-data ($^{13}$C; non-corrected): Monosaccharide-part of the product: 173.63 (C=O), 102.66 (C-1), 57.38 (C-2), 77.90 (C-3), 72.13 (C-4),76.09 (C-5), 62.79 (C-6); Aglycon part of the product: 173.65 (C-1), 35.07 (C-2), 25.72 (C-3), 26.60 (C-4), 30.24 (C-5), 70.25 (C-6) 61.38 (C-1'), 14.53 (C-2'). Selected $^1$H-data; non-corrected: 4.79 (d, H-1, $J_{1,2}$=8.1), 1.97 (s, NHAc), 1.23 (t, CH$_3$i, $J_{1',2'}$=7.3).

2. Synthesis of GlcNAcβ1-3(6-OBn)Galβ-SEt

GlcNAcβ-PNP (5 g) and (6-OBn)Galβ-SEt (5.5 g) were mixed in 0.2 M sodium phosphate buffer (150 ml, pH 7). A β-D-glucosaminidase preparation from *Aspergillus oryzae* (8 g) was added and the reaction was allowed to run at r.t. during 150 min., when about 60 mM PNP had been released, i.e. about 60% of the donor had reacted, 3 g). The mixture was filtered, extracted with metylene chloride at pH 4 (PNP removed), EtOAc (3×150 ml), which gave pure unreacted (6-OBn)Galβ-SEt, and the water phase was after concentration applied on a column containing Sephadex G10 (1 l) and was eluted with distilled water. The product containing fractions were finally purified by chromatography (silica; C:M:H; 7:3:0.3). After evaporation and drying at reduced pressure, a pure product was obtained (150 mg, white firm material; 5% w/w of reacted donor). 13C NMR data of peracetylated product (CD$_3$OD): 15.20, 24.86 (C-SEt), 56.1 (C-2'), 62.84 (C-6'), 70.21 (2C, C-2, C-4'), 71.88 (C-4), 72.67 (C-5'), 73.38 (C-3'), 74.36 (C-6, CH2Ph), 77.67 (C-3), 79.50 (C-5), 84.79 (C-1), 101.93 (C-1'), 128.75, 128.99, 129.38, 139.45 (6C, Ph), 171.09–173.12 (6C=O).

3. Synthesis of peracetylated Galα1-3Galβ-SEt and peracetylated Galα1-3Galβ-SPh

Galα-OPhOMe-p (20 g) was dissolved in 0.1 M sodium phosphate buffer (200 ml, pH 6.5). An α-D-galactosidase-preparation from coffee beans (2 g; prepared by grinding of Kenya coffee beans, extraction of the enzyme with buffer, see above, precipitation with 70% ammonium sulphate, dialysis and freeze-drying) was added and the reaction was allowed to run at 45 degrees Celsius during twenty-four hours when the major part of the substrate was reacted. It was extracted with metylene chloride at pH 4 (HOPhOMe-p removed), EtOAc (part of unreacted Galα-OPhOMe-p in the EtOAc phase), and a mixture of EtOAc and n-butanol (a mixture of remaining Galα-OPhOMe-p, of Galα-Galα-OPhOMe-p regioisomers and some of the galactose were in the organic phase). The latter organic phase was, after evaporation and dissolution in water, purified by Sephadex G10 (1.2 liter) and was eluted with distilled water. This gave pure Galα1-3Galα-OPhOMe-p (2 g; all the product was not purified), which then was used for chemical transformation (peracetylation followed by reaction with aliphatic or aromatic thiol compound, respectively) to give peracetylated Galα1-3Galβ-SEt and peracetylated Galα1-3Galβ-SPh, respectively.

Alternatively the above products were prepared via Galα1-3Galα-OPhNO$_2$-p, (which was obtained in the same way as Galα1-3Galα-OPhOMe-p, using the corresponding enzymatic reaction as above, but with Galα-OPhNO$_2$-p as substrate), which was reduced to Galα1-3Galα-OPhNH$_2$-p, peracetylated, —OPhNHAc-p was removed with CAN in acetonitrile:water to give peracetylated Galα1-3Galα,β-OH, which was transformed to peracetylated Galα1-3Galβ-SEt or peracetylated Galα1-3Galβ-SPh, respectively, via peracetylated Galα1-3Galβ-OC(=NH)CCl$_3$ followed by reaction with the respective aliphatic or aromatic thiol compound.

4. Preparation of Galα1-3Galα-OPhNH—CO-Sepharose and Galα1-3Galα-OPhNH—CO-Cellulose, Respectively Galα1-3Galα-OPhNH$_2$-p obtained as above (e.g. 1, 2, 3, 4, 5, 6, 7 or 8 mg/ml activated gel) was reacted with DSC-activated (activated with Di-N-succimidyl-carbonate, DSC, in acetone with pyridine as catalyst; DSC is analogous to N-hydroxysuccinimide, NHS) COOH-Sepharose® (Cl-6B, or 4 FF, Pharmacia), at room temperature during 2 hours, pH 8, and was treated with Tris-HCl, 0.2 M, pH 8 at room temperature during 2 hours. The material was washed with 0.1 M sodium phosphate buffer, pH 7.0, and used for separation of antibodies against the Galα1-3Gal epitope. The corresponding procedure was used for DSC-activated (activated with Di-N-succimidyl-carbonate, DSC, in acetone with pyridine as catalyst, DSC is analogous to N-hydroxysuccinimide) COOH-Cellulose from Whatman (0.1 meq COOH/g dry weight), and the resulting material was used for separation of antibodies against the Galα1-3Gal epitope.

5. Preparation of Galα1-3Galβ-1-4GlcNAcβ-O(CH$_2$)$_2$—Ph—NH$_2$ and Galα1-3Galβ1-4GlcNAcβ-O(CH$_2$)$_2$—Ph—NH—CO-Sepharose, and Galα1-3Galβ1-4GlcNAcβ-O(CH$_2$)$_2$—Ph—NH—CO-Cellulose, Respectively Peracetylated Galα1-3Galβ-SEt was reacted for example with (6-OBenzoyl)GlcNPhthβ-O(CH$_2$)$_2$—Ph—NO$_2$ in the presence of for example Ag-triflate in dichloromethane (alternatively acetonitrile) and the resulting (2,3,4,6-OAc)Galα1-3(2,4,6-OAc)Galβ1-4(6-OBensoyl)GlcNPhthβ-O(CH$_2$)$_2$—Ph—NO$_2$ was deacetylated and debenzoylated, and dephthalylated, the amino group was acetylated and the nitro group was reduced, which gave Galα1-3Galβ1-4GlcNAcβ-O(CH$_2$)$_2$—Ph—NH$_2$. Instead of acetylation of the amino group this can be reacted with other organic or inorganic substances (see the description above) and with this products of the type Galα1-3Galβ1-4GlcNRβ-O(CH$_2$)$_2$—Ph—NH$_2$ can be obtained, where R is an organic or inorganic substance. A certain amount of the regioisomer Galα1-3Galβ1-3GlcNAcβ-O(CH$_2$)$_2$—Ph—NO$_2$ is obtained together with Galα1-3Galβ1-4GlcNAcβ-O(CH$_2$)$_2$—Ph—NO$_2$ before the reduction above, which can be separated by using, for example Sephadex G10 or G15 column chromatography (water as eluent). Part of the Galα1-3Galβ1-4GlcNAcβ-O(CH$_2$)$_2$—Ph—NH$_2$ (e.g. 1,2,3 or 4 mg/ml activated gel) was reacted with DSC-activated (activated with Di-N-succimidylcarbonate, DSC, in acetone with pyridine as catalyst, DSC is analogous to N-hydroxysuccinimide) COOH-Sepharose® (Cl-6B, or 4 FF, Pharmacia), at room temperature during 2 h, pH 8, and was treated with Tris-HCl, 0.2 M, pH 8 at room temperature during 2 h. The material was washed with 0.1 M sodium phosphate buffer, pH 7.0 and was used for separation of antibodies against the Galβ1-3Gal epitope. A corresponding procedure was used for DSC-activated (activated with Di-N-succimidylcarbonate, DSC, in acetone with pyridine as catalyst, DSC is analogous to N-hydroxysuccinimide) COOH-Cellulose from Whatman (0.1 meq COOH/g dry weight), and the resulting material was used for separation of antibodies against the Galα1-3Gal epitope.

6. Preparation of Galα1-3Galβ-1-4GlcNAcβ-O(CH$_2$)$_2$—Ph—NH, and Galα1-3Galβ1-4GlcNAcβ-O(CH$_2$)$_2$—Ph—NH—CO-Sepharose, and Galα1-3Galβ1-4GlcNAcβ-O(CH$_2$)$_2$—Ph—NH—CO-Cellulose, respectively. Galα1-3Galβ-1-4GlcNAcβ-OPh—NH$_2$ and Galα1-3Galβ1-4GlcNAcβ-OPh—NH—CO-Sepharose, and Galα1-3Galβ1-4GlcNAcβ-OPh—NH—CO-Cellulose, Respectively Peracetylated Galα1-3Galβ-SEt was reacted for example with (6-OBenzoyl)GlcNAcβ-OPh—NO$_2$-p in the presence of for example Ag-triflate in dichloromethane (alternatively acetonitrile) at low temperature (for example −40 degrees Celsius) and the resulting (2,3,4,6-OAc)Galα1-3(2,4,6-OAc)Galβ1-4(6-OBenzoyl)GlcNAcβ-OPh—NO$_2$-p was deacetylated and debenzoylated and the nitro group was reduced, which gave Galα1-3Galβ1-4GlcNAcβ-OPh—NH$_2$. A certain amount of the regioisomer Galα1-3Galβ1-3GlcNAcβ-OPh—NO$_2$ is obtained together with Galβ1-3Galβ-4GlcNAcβ-OPh—NO$_2$ before the reduction above, which can be separated away if desired, with for example Sephadex G10 or G15 column chromatography (water as eluent). Part of Galα1-3Galβ1-4GlcNAcβ-OPh—NH$_2$ (e.g. 1, 2, 3 or 4 mg/ml activated gel) with DSC-activated (activated with Di-N-succimidylcarbonate, DSC, in acetone with pyridine as catalyst, DSG is analogous to N-hydroxysuccinimid) COOH-Sepharose® (Cl-6B, or 4FF, Pharmacia), at room temperature during 2 h, pH 8, and was treated with Tris-HCl, 0.2 M, pH 8, at room temperature during 2 h. The material was washed with 0.1 M sodium phosphate buffer, pH 7.0 and was used for separation of antibodies against the Galα1-3Gal epitope. A corresponding procedure was used for DSC-activated (activated with Di-N-succimidylcarbonate, DSC, in acetone with pyridine as catalyst; DSC is analogous to N-hydroxysuccinimide) COOH-Cellulose from Whatman (0.1 meq COOH/g dry weight), and the resulting material was used for separation of antibodies against the Galα1-3Gal epitope.

7. Preparation of
   a) Galα1-3Galβ-1-4GlcNAcβ1-3Gal,
   b) Galα1-3Galβ-1-4GlcNAcβ1-3Galβ-O(CH$_2$)$_2$—Ph—NH$_2$-p and
   c) Galα1-3Galβ-1-4GlcNAcβ1-3Galβ-OPh—H$_2$-p
   d) Galα1-3Galβ1-4GlcNAcβ1-3Galβ-O(CH$_2$)$_2$—Ph—NH—CO-Sepharose, and,
   e) Galα1-3Galβ1-4GlcNAcβ1-3Galβ-O(CH$_2$)$_2$—Ph—NH—CO-Cellulose respectively, and
   f) Galα1-3Galβ1-4GlcNAcβ1-3Galβ-OPh—NH—CO-Sepharose respectively
   g) Galα1-3Galβ1-4GlcNAcβ1-3Galβ-OPh—NH—CO-Cellulose.

Corresponding reactions were used as in example 5 with a donor such as in 5 above, but instead an acceptor for example of the type (6-Obenzyl)GlcNAcβ1-3(6,2-OAc)Galβ-OCH$_2$Ph, or (6-Obenzyl)GlcNAcβ1-3(6,2-OAc)Galβ-O(CH$_2$)$_2$—Ph—NO$_2$, or (6-Obenzyl)GlcNAcβ1-3(6,2-

OAc)Galβ-OPh—NO$_2$ respectively, was used (dephthalylation and acetylation, respectively, of the free amino group was not required because there was already an N-acetyl group in the acceptor), for preparation of 6(a) (the benzyl group was removed in the final step with reduction, Pd/C), b, d and e, respectively, as well as c, f, and g, respectively.

The amino-group product was used for coupling to DSC-activated COOH-cellulose and Sepharose, respectively, according to what is mentioned above.

8. Production of Galα1-3Gal, Galα1-3Galβ-O(CH$_2$)$_2$PhNH$_2$ and Immobilised Galα1-3Galα-OPhNH$_2$ and Galα1-3Galβ1-4GlcNAcβ-OPhNH$_2$ Galα-OPhNO$_2$-p (20 g) was dissolved in 0.1 M sodium hydrogen phosphate buffer, pH 6.5, and freeze-dried α-galactosidase-preparation (2 g, from ground coffee beans, prepared by extraction with buffer, dialysis and freeze-drying) was added at 45 degrees C. The reaction was allowed to run during twenty-four hours, after which the mixture was heated (inactivation of the enzyme), cooled, extracted at pH 4.5 with ethyl acetate, butanol. The butanol phase was evaporated and was purified with chromatography (Sephadex G10, water as eluent) which gave purified Galα1-3Galα-OPhNO$_2$-p (about 3 g after freeze-drying). Treatment of part of the product with, in sequence, H$_2$/Pd/C, Ac$_2$O/Pyridine, CAN/Acetonitrile-water, gave (Ac)$_7$Galα1-3Gal-OH (75% yield, based on mole starting material) which after conventional deacetylation gave Galα1-3Gal, which was pure according to NMR. The treatment of (Ac)$_7$Galα1-3Gal-OH with, in sequence, Cl$_3$CCN/NaH/dichloromethane, HO(CH$_2$)$_2$PhNO$_2$-p/dichloromethane-acetonitrile/TMSOtriflate, gave (Ac)$_7$Galα1-3Galα-O(CH$_2$)$_2$PhNO$_2$-p. Deacetylation with NaOMe/MeOH and reduction of the nitro group with H$_2$/Pd/C in MeOH water, gave Galα1-3Galα-O(CH$_2$)$_2$PhNH$_2$-p, which was pure according to NMR. The latter substance was immobilised to DSC-activated (activated with Di-N-succimidylcarbonate, DSC, in acetone with pyridine as catalyst, DSC is analogous to N-hydroxysuccinimide). COOH-Sepharose® (Pharmacia) and was used for separation of antibodies against the Galα1-3Gal epitope. Galα1-3Galα-OPhNH$_2$ produced after the H$_2$/Pd/C step above and Galα1-3Galβ1-4GlcNAcβ-OPhNH$_2$, were immobilised to NHS-activated Sepharos 4 FF according to the description above.

9. Preparation of a) Galα1-3Galα-OPh—NH—CO-PEG b) (Galα1-3Galα-OPh—NH—CO)$_2$-PEG c) (Galα1-3Galα-OPh—NH—CO)$_n$-PEG d) Galα1-3Galβ1-4GlcNAcβ-OPh—NH—CO-PEG e) (Galα1-3Galβ1-4GlcNAcβ-OPh—NH—CO)$_2$-PEG f) (Galα1-3Galβ1-4GlcNAcβ-OPh—NH—CO)$_n$-PEG g) Galα1-3Galβ1-4GlcNAcβ1-3Galβ-OPh—NH—CO-PEG i) (Galα1-3Galβ1-4GlcNAcβ1-3Galβ-OPh—NH—CO)$_2$-PEG j) GlcNAcβ1-3Galβ-O(CH$_2$)$_2$—Ph—NH—CO-PEG k) (GlcNAcβ1-3Galβ-O(CH$_2$)$_2$—Ph—NH—CO)$_2$-PEG l) (GlcNAcβ1-3Galβ-O(CH$_2$)$_2$—Ph—NH—CO)$_n$-PEG m) Galβ1-3GlcNAcβ1-3Galβ-O(CH$_2$)$_2$—Ph—NH—CO-PEG h) (Galβ1-3GlcNAcβ1-3Galβ-O(CH$_2$)$_2$—Ph—NH—CO)$_2$-PEG i) (Galβ1-3GlcNAcβ1-3Galβ-O(CH$_2$)$_2$—Ph—NH—CO)$_n$-PEG To obtain the above types of products, the corresponding di-, tri-, or tetrasaccharide was reacted with Methoxy-SPA-PEG (a,d,etc), SPA$_2$-PEG or Star-tresyl-PEG (available from Shearwater Polymeres, Inc, USA, the PEG-names from their catalogue). The above constitute examples only, and other types of PEG-derivative, cross-linker, or saccharides with other spacer for coupling, can be used to obtain analogous, soluble saccharide conjugates.

What is claimed is:

1. The saccharide compound Galα1-3Galβ1-4GlcNAcβ-OEtPhNH— CO(CH$_2$)$_5$NH—CH$_2$—CH(OH)—CH$_2$—O-Sepharose® 4FF.

2. A method of making the saccharide compound of claim 1 comprising:

reacting carbohydrate —OCH$_2$CH$_2$PhNH$_2$ with NHS-activated Sepharose 4FF to obtain the desired product.

3. A method of making the saccharide compound of claim 1 comprising:

reacting Galα1-3Galβ1-4GlcNAcβ-OPHNH$_2$ with NHS-activated Sepharose-4FF.

4. A method for the treatment of a patient in connection with and after xenotransplantation of an organ in said patient comprising contacting plasma of the patient with the saccharide compound of claim 1 for the elimination of antibodies against said saccharide compound from the plasma.

5. A method for the removal of at least one of cells, proteins and enzymes from a plasma sample taken from a patient in need thereof comprising contacting said plasma sample with the saccharide compound of claim 1 and thereby isolating or removing said at least one of said cells, proteins and enzymes.

6. The method according to claim 5 wherein glycosyltransferases, lectins or antibodies are isolated.

7. A method for the diagnosis for the presence of at least one member of the group consisting of bacteria, cells, enzymes, anti-bodies and carbohydrate bound proteins having specificity towards a saccharide in a body fluid from a patient in need of said diagnosis comprising contacting said fluid with the saccharide compound of claim 1.

8. The method according to claim 7 wherein said saccharide is present in a biosensor or in an ELISA.

* * * * *